United States Patent [19]

Rando

[11] Patent Number: 5,789,541
[45] Date of Patent: Aug. 4, 1998

[54] COMPOUNDS FOR INHIBITION OF PROTEOLYSIS

[75] Inventor: Robert R. Rando, Newton Centre, Mass.

[73] Assignee: President and Fellows of Harvard College, Cambridge, Mass.

[21] Appl. No.: 362,605

[22] PCT Filed: Jul. 14, 1993

[86] PCT No.: PCT/US93/06593

§ 371 Date: Feb. 13, 1995

§ 102(e) Date: Feb. 13, 1995

[87] PCT Pub. No.: WO94/01126

PCT Pub. Date: Jan. 20, 1994

Related U.S. Application Data

[63] Continuation-in-part of Ser. No. 914,164, Jul. 14, 1992, abandoned.

[51] Int. Cl.[6] ............................................. A61K 38/03
[52] U.S. Cl. ...................... 530/326; 530/330; 530/331; 514/13; 514/18
[58] Field of Search ................................. 530/326, 330, 530/331; 514/18, 13

[56] References Cited

PUBLICATIONS

Tan et al., J. Am. Chem. Society (113), pp. 6299–6300, Jul. 31, 1991.
Hancock et al., Cell 57:1167, 1989.
Gutierrez et al., EMBO J. 8:1093, 1989.
Willumsen et al., EMBO J. 3:2581 (date unknown).
Lai et al., Proc. Nat'l. Acad. Sci. USA 87:7673, 1990.
Anderegg et al., J. Biol. Chem. 263:18236, 1988.
Chelsky et al., J. Biol. Chem. 262:4303, 1987.
Farnsworth et al., J. Biol. Chem. 264:20422, 1989.
Vorburger et al., EMBO J. 8:4007, 1989.
Hancock et al., EMBO J. 10:641, 1991.
Maltese et al., J. Cell Physiol. 125:540, 1985.
Sinensky et al., Proc. Nat'l. Acad. Sci. USA 82:3257, 1985.
Beck et al., J. Cell Biol. 107:1307, 1988.
Ashby et al., Proc. Nat'l. Acad. Sci. USA 89:4613, 1992.
Walter et al., Meth. Enzym. 96:84, 1983.
Perez-Sala et al., Proc. Nat'l. Acad. Sci. USA 88:3043, 1991.
Trepman et al., Arch. Biochem. Biophys. 204:524, 1980.

*Primary Examiner*—Jerry D. Johnson
*Attorney, Agent, or Firm*—Fish & Richardson P.C.

[57] ABSTRACT

This invention features compounds of the formula: W—Y—$CH_2$—Q wherein W is a farnesyl group, a geranylgeranyl group, a substituted farnesyl group or a substituted geranylgeranyl group or a lipophilic unsaturated hydrocarbon; Y is: —S—, —O—, —Se—, (I), (II), (III), (IV), (V) or —$CH_2$—; Q is (VI) wherein $T_1$ is: H, F, or —$(CH_2)_n$—$X_1$; $T_2$ is: —$NHCOCH_3$, —$NH(CH_2)_n$—$X_1$, (VII) or a peptide of 20 or fewer amino acids; wherein $X_1$ is: —SH, —COOH, or —$CONH_2$; and n is an integer less than 20; $T_3$ is: (VIII), (IX), (X), (XI), (XII), (XIII), (XIV), —$CH_2$—$X_2$, (XV), (XVI), or —$CF_2$—$X_2$ wherein $X_2$ is a peptide of 20 or fewer amino acids linked to carbon via the amino terminal nitrogen of said peptide; $X_3$ is a peptide of 20 or fewer amino acids linked via an alpha carbon of said peptide; and n is an integer less than 20, said compound being characterized by inhibiting enzymatic proteolysis of a peptide having the carboxyl—terminal motif —CAAX wherein C=cysteine, A=aliphatic amino acid, and X=any amino acid.

16 Claims, 13 Drawing Sheets

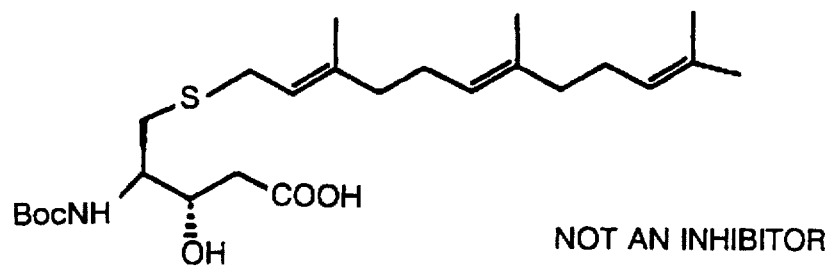
NOT AN INHIBITOR
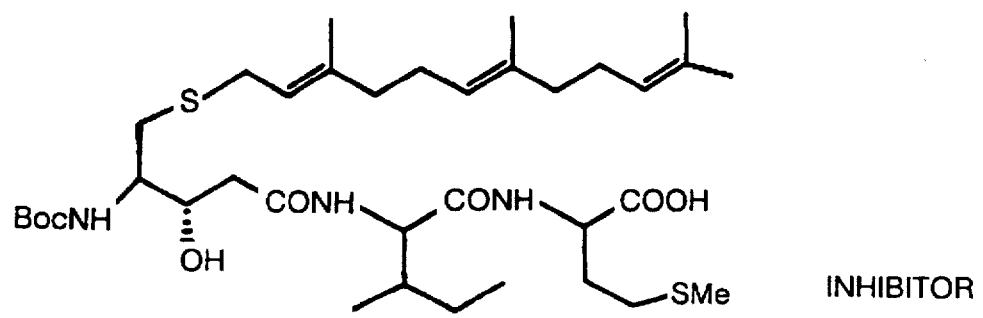
INHIBITOR
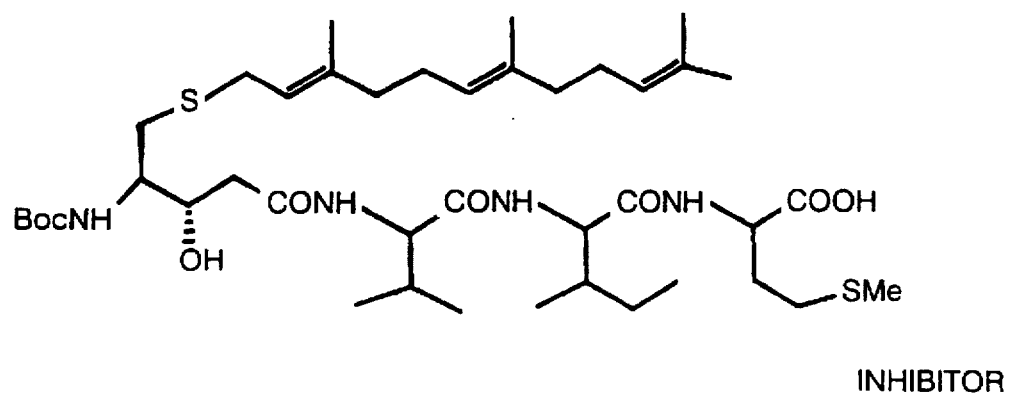
INHIBITOR
FIG. 5 (PAGE 1 OF 2)

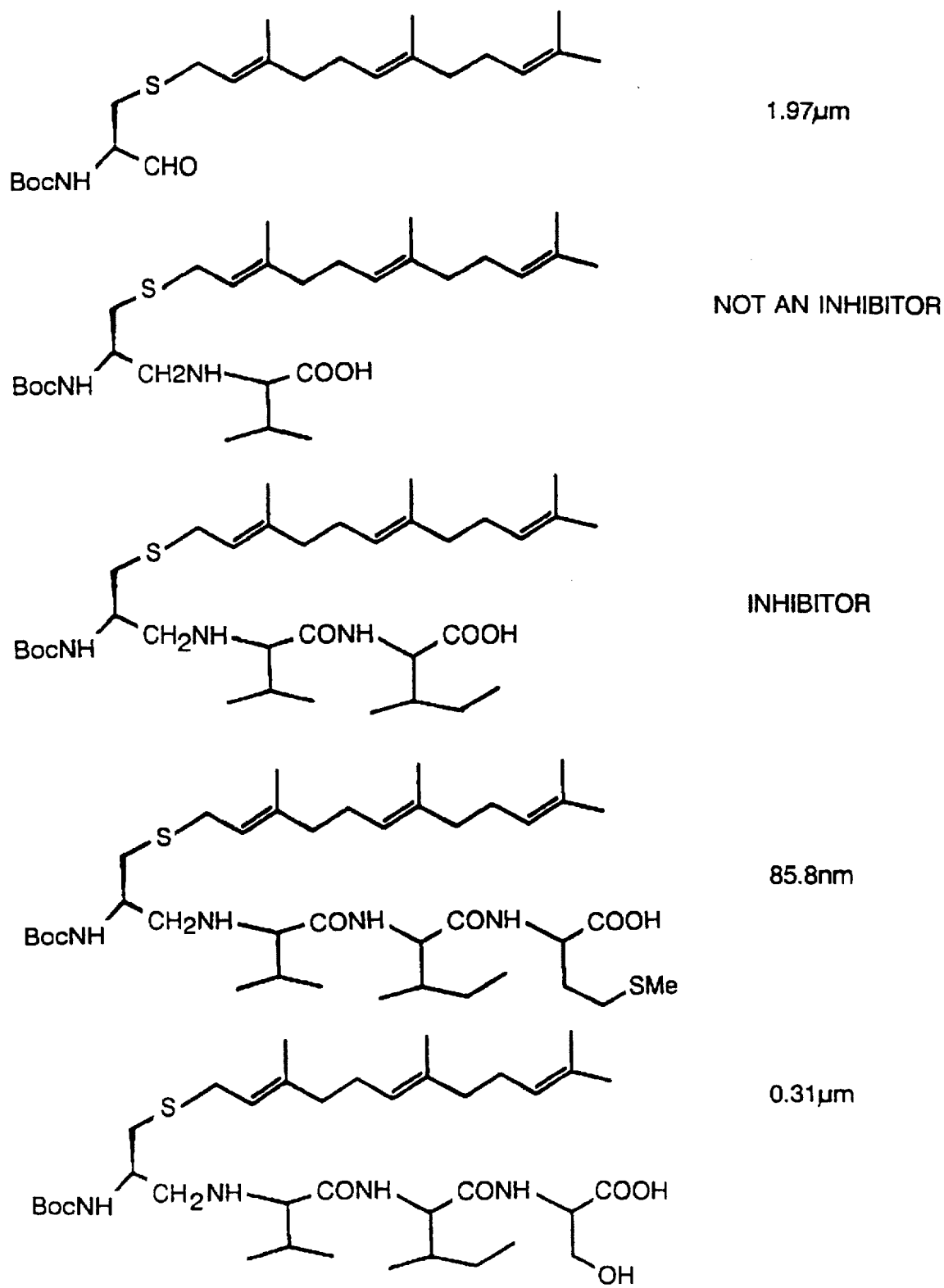
FIG. 5 (PAGE 2 OF 2)

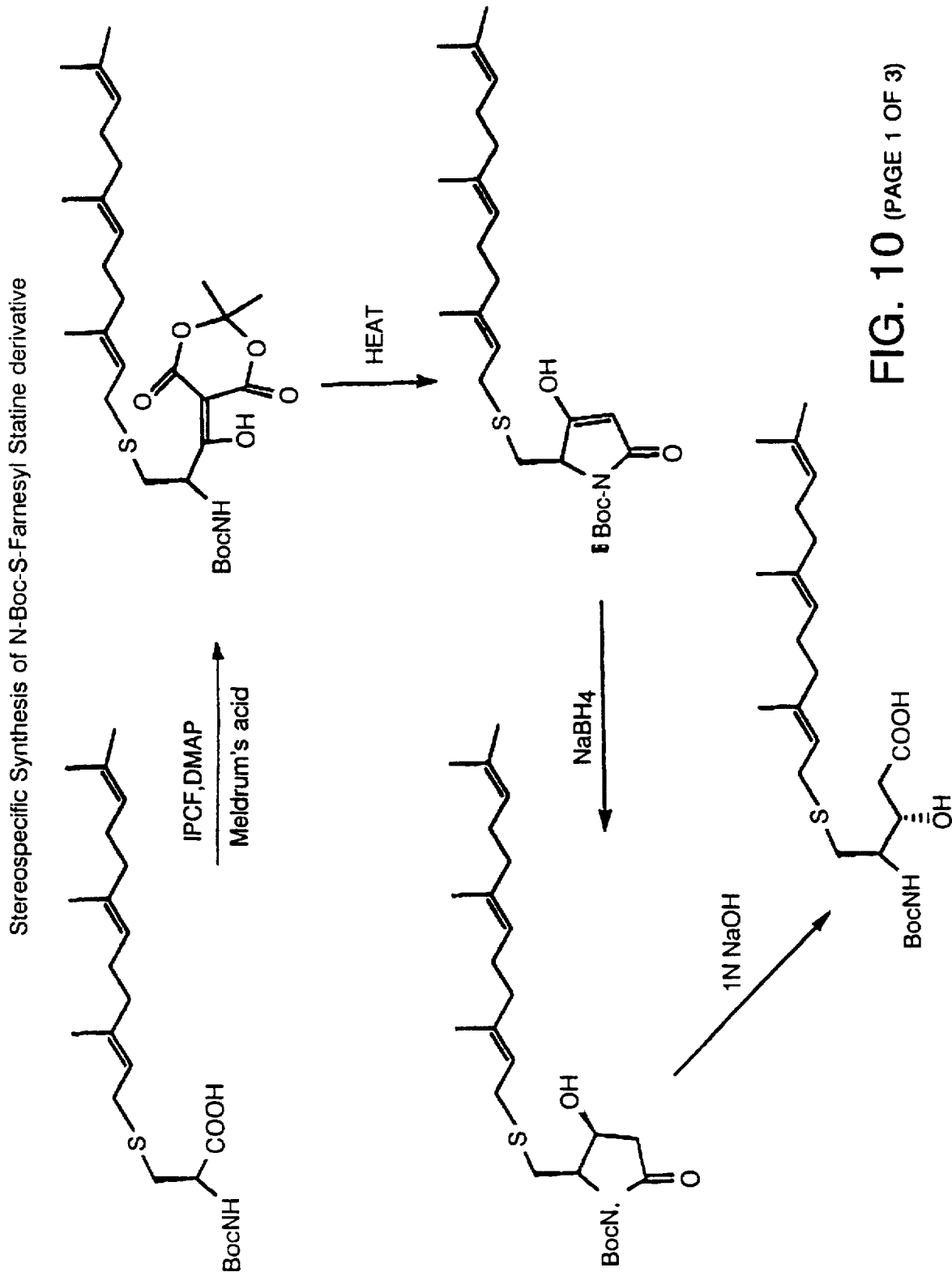
FIG. 10 (PAGE 1 OF 3)

(PAGE 2 OF 3)

(PAGE 3 OF 3)

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 4 amino acids
( B ) TYPE: amino acid
( C ) STRANDEDNESS: Not Relevant
( D ) TOPOLOGY: linear ( x i ) SEQUENCE DESCRIPTION: SEQ ID NO:1:

Cys Val Ile Ser
1

( 2 ) INFORMATION FOR SEQ ID NO:2:

( i ) SEQUENCE CHARACTERISTICS:
( A ) LENGTH: 4 amino acids
( B ) TYPE: amino acid
( C ) STRANDEDNESS: Not Relevant
( D ) TOPOLOGY: linear ( x i ) SEQUENCE DESCRIPTION: SEQ ID NO:2:

Cys Val Ile Met
1

( 2 ) INFORMATION FOR SEQ ID NO:3:

( i ) SEQUENCE CHARACTERISTICS:
( A ) LENGTH: 4 amino acids
( B ) TYPE: amino acid
( C ) STRANDEDNESS: Not Relevant
( D ) TOPOLOGY: linear ( x i ) SEQUENCE DESCRIPTION: SEQ ID NO:3:

Cys Ala Ala Xaa
1

COMPOUNDS FOR INHIBITION OF PROTEOLYSIS

This us a continuation-in-part of the national phase of my PCT application PCT US93/0659, filed Jul. 14, 19993, which in turn was a continuation-in-part if U.S. Ser. No. 07/914,164 filed on Jul. 14, 1992, now abandoned. Each of these applications is hereby incorporated by reference.

This invention is supported by NIH Grant No. EY03634 and the government has certain rights to the invention.

BACKGROUND OF THE INVENTION

This invention relates to controlling neoplastic cell growth. This invention is supported by NIH Grant No. EY03624 and the government has certain rights to the invention.

Activated ras genes have been associated with a number of human cancers. An activated ras gene, H-ras-1, was the first non-viral oncogene discovered. Several other human ras proto-onco genes have subsequently been identified including H-ras-2, K-ras-1, K-ras-2, and N-ras. For each of these ras genes several activated mutant forms have been identified. Activated K-ras genes have been detected in pre-malignant neoplasms of the human colon and in human pre-leukemia.

The ras proteins, and ras-like proteins, as well as other proteins such as signal transducing G proteins, have a conserved carboxyl-terminal -CAAX motif (C=cysteine, A=aliphatic amino acid, and X=any amino acid)(SEQ ID No. 3). This motif is involved in a series of post-translational modifications including polyisoprenylation carboxyl-terminal proteolysis, and carboxyl-methylation. A number of ras-related small GTP binding proteins including R-ras, RAS2, rap-2, and phoB also have a carboxyl-terminal -CAAX motif, and it has been suggested that these proteins may be post-translationally modified in the same manner (Hancock et al., *Cell* 57:1167, 1989). Among ras proteins, H-ras, N-ras (Gutierrez et al., *EMBO J.*, 8:1093, 1989) and K-ras (Hancock et al., Cell, 57:1167, 1989) undergo polyisoprenylation, carboxyl-terminal proteolysis and carboxyl-methylation. Inhibition of these modifications by mutation of Cys[186] to Ser blocks both membrane localization of ras gene product and transformation of the cell (Willumsen et al., *EMBO J.* 3:2581; Gutierrez et al., *EMBO J.* 8:1093, 1989).

A number of other proteins which have a carboxyl-terminal -CAAX motif including the γ-subunit of transducing (Lai et al., *Proc. Natl. Acad. Sci. USA*, 87:7673, 1990), yeast mating factor mata (Anderegg et al., *J. Biol. Chem.*, 263:18236, 1988), and nuclear lamin B (Chelsky et al., *J. Biol. Chem.*, 262:4303, 1987; Farnsworth et al., *J. Biol. Chem.*, 264:20422, 1989; Vorburger et al., *EMBO J.*, 8:4007, 1989) have also been shown to undergo polyisoprenylation, carboxyl-terminal proteolysis, and carboxyl-methylation.

Analysis of in vitro translated K-ras demonstrated,d that farnesylated, non-proteolysed, non-methylated K-ras associates inefficiently with cell membranes. Removal of the carboxyl-terminal three amino acids of this K-ras product increases membrane binding 2-fold, and methylation of the K-ras product increases membrane binding another two-fold (Hancock et al., *EMBO J.* 10:641 1991).

Mevinolin inhibits cellular synthesis of mevalonic acid; this leads to depletion of polyisoprenoids and is expected to interfere with polyisoprenylation reactions. Mevinolin affects post-translational processing of ras proteins and interferes with ras membrane localization (Hancock et al., *Cell* 57:1167, 1989). In addition, cells treated with mevinolin are blocked in cell growth in the G1 phase and the G2/M phase (Maltese et al., *J. Cell Physiol.* 125:540, 1985). It has been proposed that this growth arrest, which is associated with the inhibition of mevalonate incorporation into polypeptides but not other isoprenoid derivatives such as cholesterol (Sinensky et al., *Proc. Natl. Acad. Sci. USA*, 82:3257, 1985), is caused by disruption of nuclear lamin B function (Beck et al., *J. Cell. Biol.*, 107:1307, 1988). The observation that mevinolin interferes with post-translational modification of the ras gene product combined with involvement of activated ras genes in human malignancies has led to the suggestion that mevinolin or derivatives of mevinolin may prove to be novel cytotoxic/static agents or even a starting point for the development of an anti-ras drug (Hancock et al., *Cell* 57:1167, 1989).

Hancock et al. (*EMBO J.* 10:641, 1991) report that a proteolytic activity capable of removing the -AAX motif of $p21^{K-ras(B)}$ is associated with microsomal membranes.

Ashby et al. (*Proc. Nat'l. Acad. Sci. USA* 89:4613, 1992) report that yeast have three proteolytic activities which, when incubated with farnesylated yeast a-factor octapeptide, release the terminal three amino acids as a tripeptide.

SUMMARY OF THE INVENTION

In general, the invention features certain novel compounds which inhibit carboxy terminal proteolysis of proteins having a carboxyl-terminal -CAAX motif (C=cysteine, A=aliphatic amino acid, and X=any amino acid)(SEQ ID NO: 3).

In general, the invention features compounds having the formula W—Y—CH$_2$—Q wherein W is a farnesyl group, a geranylgeranyl group, a substituted farnesyl group or a substituted geranylgeranyl group; Y is:

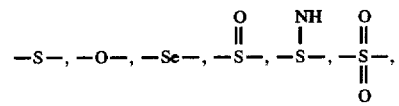

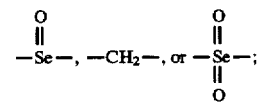

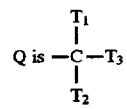

$T_1$ is: H, F, or —(CH$_2$)$_n$—X$_1$;

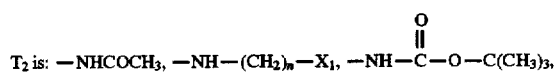

or a peptide of 20 or fewer amino acids, preferably 15 or fewer amino acids, more preferably 10 or fewer amino acids, even more preferably 5 or fewer amino acids, still more preferably 3 or fewer amino acids, linked to carbon via the amino terminal nitrogen of the peptide, and n is an integer less than 20, preferably less than 10, more preferably less than 5, still more preferably less than 3, yet more preferably 1 or 2; wherein X$_1$ is: —SH, —COOH, —CONH$_2$

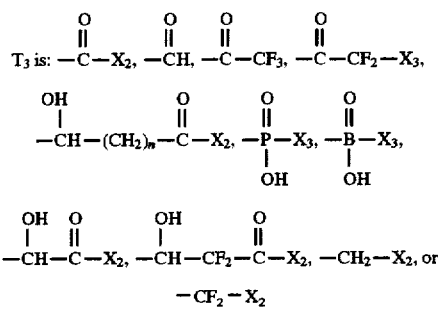

wherein $X_2$ is a peptide of 20 or fewer amino acids, preferably 15 or fewer amino acids, more preferably 10 or fewer amino acids, even more preferably 5 or fewer amino acids, still more preferably 3 or fewer amino acids, linked to carbon via the amino terminal nitrogen of the peptide, n is an integer less than 20, preferably less than 10, more preferably less than 5, still more preferably less than three, yet more preferably 1 or 2; $X_3$ is a peptide of 20 or fewer amino acids, preferably 15 or fewer amino acids, more preferably 10 or fewer amino acids, even more preferably 5 or fewer amino acids, still more preferably 3 or fewer amino acids, yet more preferably 1 or 2 amino acids, linked to carbon via the alpha carbon of one of the amino acids of the peptide, preferably the amino terminal amino acid of the peptide.

Regarding the farnesyl and geranylgeranyl moieties, hydrogen may generally be replaced by fluorine and a methyl group may generally be replaced by a bromine. Accordingly, "substituted farnesyl group" means a farnesyl moiety in which one or more hydrogens have been replaced by fluorine or one or more methyl groups have been replaced by a bromine, and "substituted geranylgeranyl group" means a geranylgeranyl moiety in which one or more hydrogens have been replaced by fluorine or one or more methyl groups have been replaced by bromine.

In addition, the farnesyl or geranylgeranyl group may be replaced by a structurally related moiety. Such related moieties include generally lipophilic hydrocarbons including group of aromatic rings. Preferred hydrocarbons include 5 to 15, preferably 10 carbons. Preferred moieties are those which closely resemble farnesyl in structure.

Preferred compounds include:

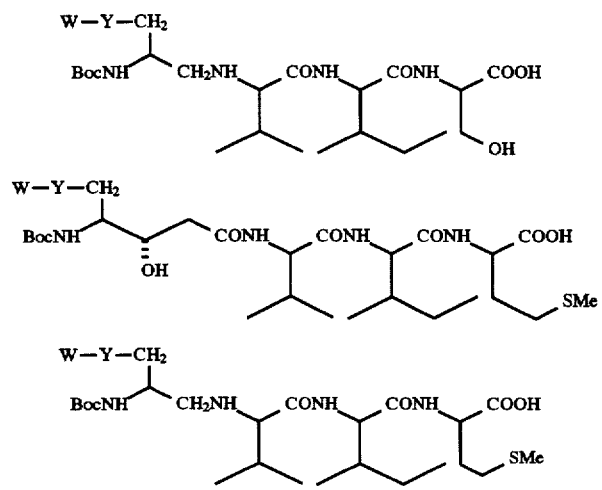

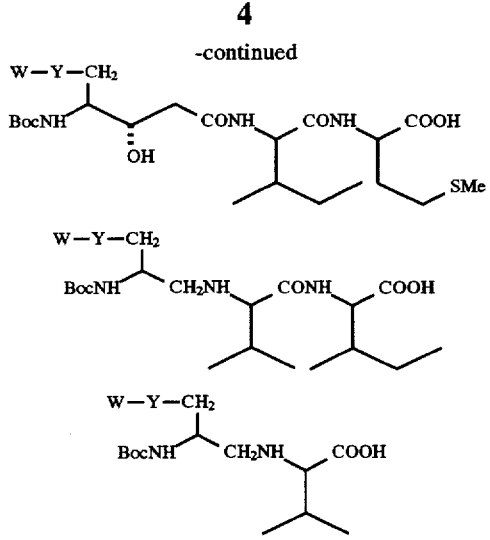

wherein BocNH is

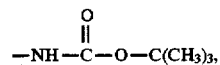

W is farnesyl, and Y is —S—.

The compounds of the invention may be either classic competitive inhibitors or, in a less preferred alternative, an enzyme substrate that has a Km low enough to cause an effective reduction in proteolysis of the normal protein substrate (e.g.,the ras gene product). Standard assays may be used to determine Km for substrates and Ki for inhibitors. Generally preferred compounds have small values of Ki or Km. The values of Ki and Km are calculated from kinetic assays by conventional means (Fersht, Enzyme Structure and Mechanism, W. H. Freeman and Co., N.Y., 1984). Examples are provided below to illustrate suitable assays, and are not intended to limit the invention.

In a related aspect, the invention features a therapeutic composition which includes the above-described compound capable of inhibiting carboxy terminal proteolysis of a protein having a carboxyl terminal -CAAX motif (SEQ IQ NO: 3).

In a related aspect, the invention features a method for controlling neoplastic cell growth in a patient. The method includes administering to the patient the a therapeutic composition comprising the above described compound.

Other features and advantages of the invention will be apparent from the following description of the preferred embodiments and from the claims.

BRIEF DESCRIPTION OF THE DRAWING

FIG. 5 is a set of schematic drawings of various inhibitors and, for some the measured Ki.

DESCRIPTION OF THE PREFERRED EMBODIMENTS(S)

Figure 1:
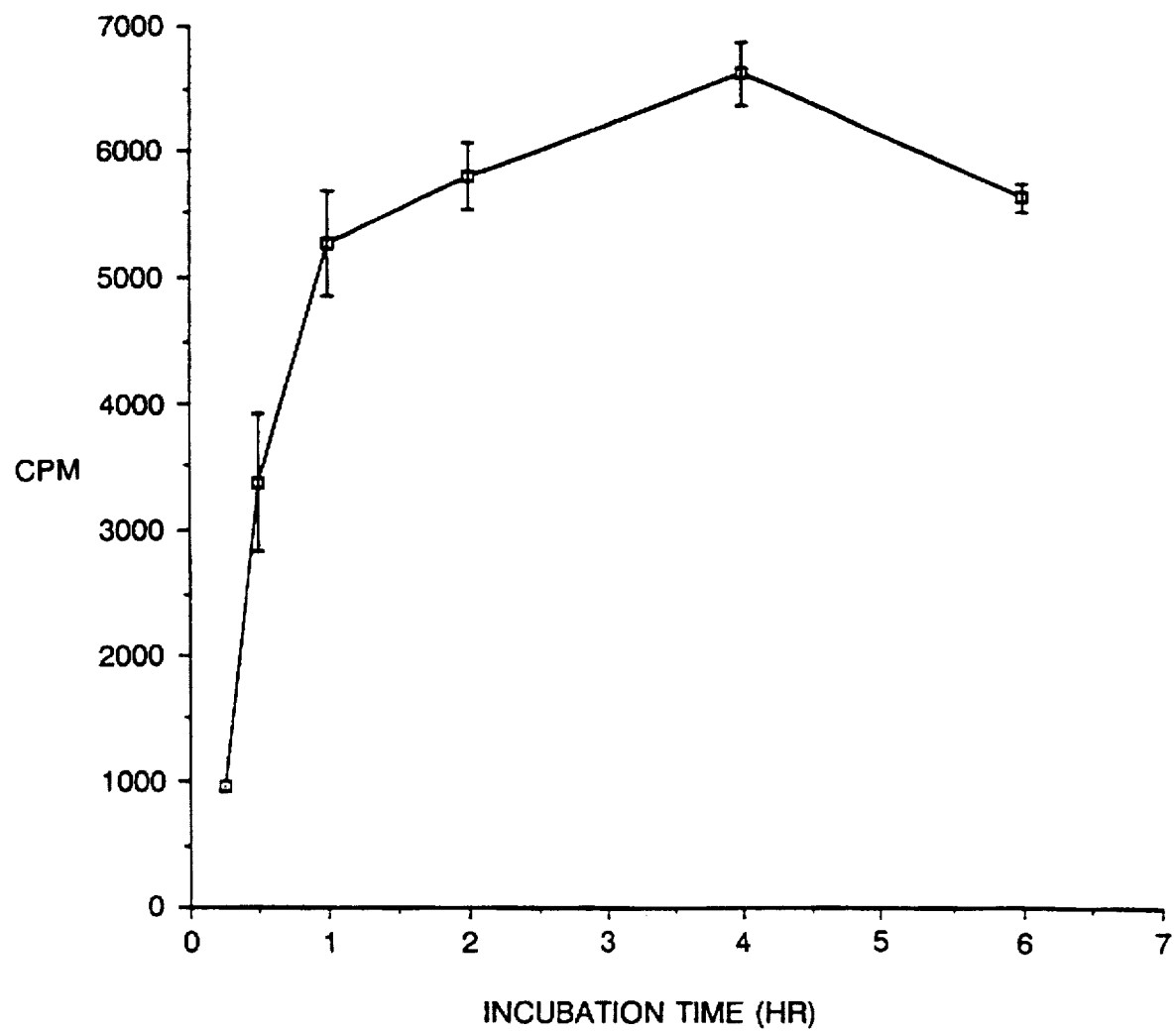
FIG. 1 is a graph which illustrates the time-dependent hydrolysis of N-[$^3$H]acetyl-S-farnesyl-L-cys-L-val-L-ile-L-ser in the presence of a bovine liver microsomal membrane preparation. N-[$^3$H]acetyl-S-all-trans-farnesyl-L-cysteine released (cpm) is plotted as a function of incubation time (min).

Described below is the characterization of a microsomal enzymatic activity which can specifically cleave the tetrapeptide N-acetyl-S-farnesyl-L-cys-L-val-L-ile-L-ser or N-[$^3$H]acetyl-S-farnesyl-(SEQ ID NO: 1) between the isoprenylated cysteine residue and the valine residue. This activity is likely to be similar to the activity responsible for the carboxyl-terminal proteolysis step of the above-described post-translational modification of -CAAX motif proteins. Also described are certain compounds which are characterized by the ability to inhibit this proteolysis. The compounds may be either classic competitive inhibitors or, in a less preferred alternative, an enzyme substrate that has Km low enough to cause an effective reduction in proteolysis of the normal protein substrate (e.g. the ras gene product). Such compounds will be useful for inhibiting the activity of certain proteins, e.g., proteins. Standard assays may be used to determine km for substrates and Ki for inhibitors. Generally preferred compounds have small values of Ki or Km. The values of Ki and Km are calculated from kinetic assure by conventional means (Fersht, Enzyme Structure and Mechanism, W. H. Freeman and Co., New York, 1984). Examples are provided below to illustrate suitable assays, and are not intended to limit the invention. Also described is a method for using the microsomal enzymatic activity to screen compounds for their ability to inhibit complete post-translation modification.

For all experiments described herein amino acids and dipeptides were purchased from Bachem Inc. β-mercaptoethanol, o-phthalaldehyde, all-trans-farnesyl bromide, all-trans-farnesol, 4,4-dimethylaminopyridine, general 1-hydroxybenzotriazole hydrate, 1-(3-dimethylamino)propyl-3-ethyl carbodiimide hydrochloride, N-methylmorpholine, and 1-hydroxybenzotriazole hydrate were purchased from the Aldrich Chemical Co. All-trans-geranylgeraniol was from TCI, Inc. HPLC solvents were from J. T. Baker Inc. All chemicals and solvents purchased were of the highest purity available. [$^3$H]-L-serine and [$^3$H]-acetic anhydride were from New England Nuclear Inc.

Dog pancreatic microsomes were purchased from Promega Inc. Fresh bovine calf liver was obtained from a slaughter house. Cys-Val-Ile and t-butylthio Cys-Val-Ile were synthesized by a automated peptide synthesizer and were isoprenylated as described below.

Enzymatic Hydrolysis of a Synthetic Tetrapeptide

N-acetyl-S-farnesyl-L-cysteine-L-val-L-ile-L-ser (AFC-val-ile-ser or N-[$^3$H]acetyl-S-farnesyl-(SEQ ID NO: 1); all L amino acids; synthesis described below) 1 was chosen as a synthetic substrate for the protease. This sequence is taken from the carboxyl terminus of the γ subunit of the retinal heterotrimeric G protein transducing. The γ subunit of transducing has previously been shown to be farnesylated and methylated 30 (Fukada et al., Nature 346:658, 1990). Incubation of the above mentioned tetrapeptide (labelled with an 3H-acetyl group) with a calf liver microsomal enzyme preparation led to the time dependent formation of N-acetyl-S-all-trans-farnesyl-L-cysteine (AFC).

Figure 2:
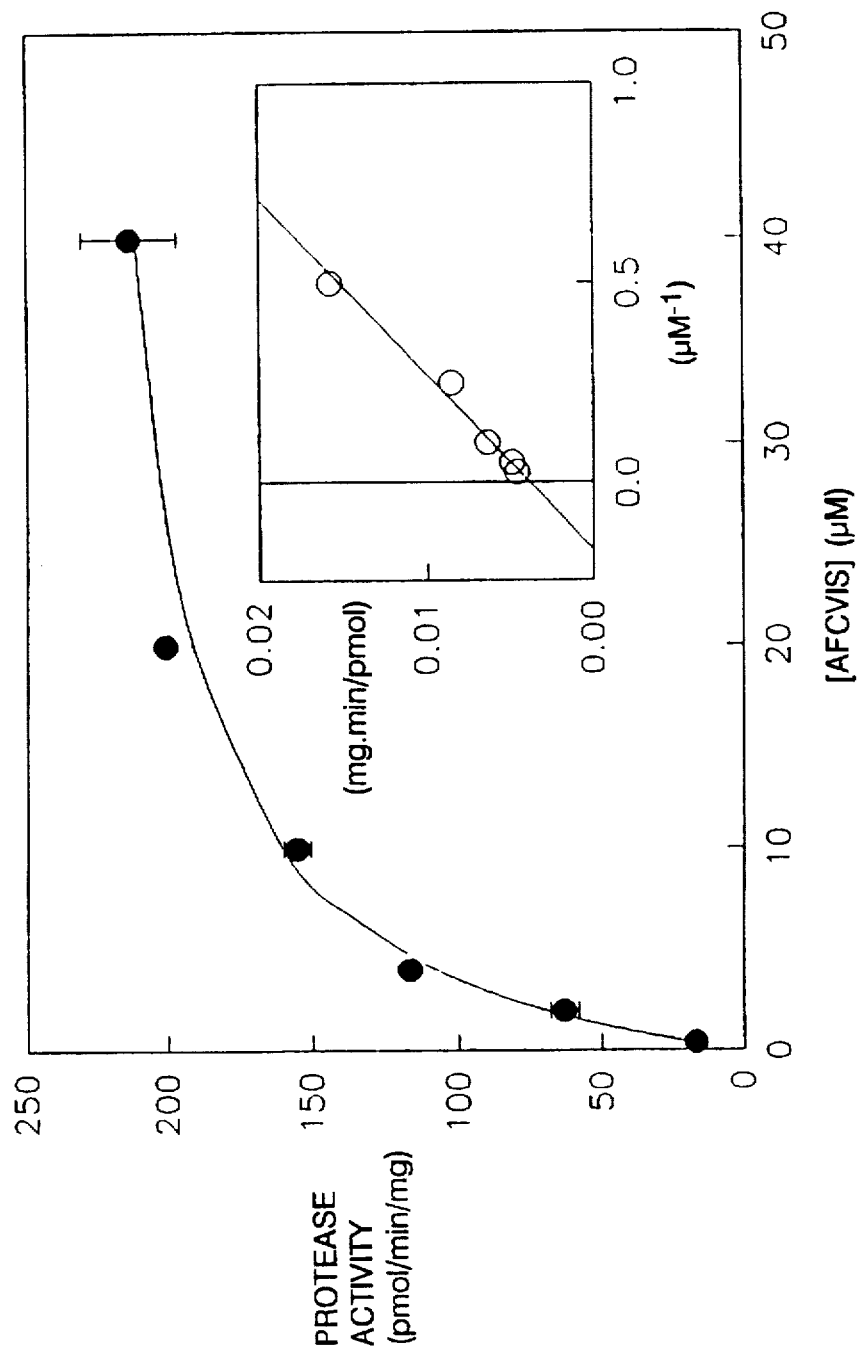
FIG. 2 is a pair of graphs illustrating the kinetics of the formation of N-[$^3$H]acetyl-S-all-trans-farnesyl-L-cysteine (N-[$^3$H]-AFC) as a function of N-[$^3$H]-acetyl-S-farnesyl-L-cys-L-val-L-ile-L-ser (AFCVIS) or N-[$^3$H]acetyl-S-farnesyl-(SEQ ID NO: 1) concentration. Protease activity (pmol/min/mg) is plotted as a function of AFCVIS concentration (μM) in panel A. Panel B is an Eadie-Hofstee plot of the same data. Symbols represent mean values of two determinations and error bars represent the standard deviation from the mean. Error bars not shown are within symbols.

Briefly, N-[$^3$H]-Acetyl-S-farnesyl-L-cys-L-val-L-ile-L-ser or N-[$^3$H]acetyl-S-farnesyl-(SEQ ID NO: 1) at a concentration of 10 µM was incubated with bovine liver microsomal membranes (preparation described below). Periodically, 50 µL aliquots were withdrawn from the incubation mixture and the reaction was quenched with 500µL of chloroform/methanol (1:1, v/v). N-[$^3$H]-AFC was extracted after thoroughly mixing the mixture for 1 minute and extracting with chloroform. Phase separation was achieved by adding 500µL of 1M citric acid. The chloroform layer was evaporated under nitrogen, resuspended in hexane/isopropanol/TFA (85:15:0.1), and authentic AFC standard was added for detection at 210 nm. The sample was injected on a silica HPLC column (Dynamax 60A, Rainin, Woburn, Mass.) and eluted with the same solvent. Radioactivity was counted with an on-line Berthold (Nashua, N.H.) LB 506-C HPLC radioactivity monitor. The results are presented in FIG. 1. When the concentration of substrate I was varied, saturation was observed, and the $K_M$ and $V_{max}$ were measured to be 4.8+0.6 µM and 0.236+0.008 nmol/min/mg protein respectively (FIG. 2).

AFC formation did not occur when the tetrapeptide was D-AFC-val-ile-ser (synthesis described below) 2, nor when the carboxyl group of the serine residue was methylated. These data demonstrate that the proteolysis is stereospecific, and that a free carboxyl terminal group is required in the substrate.

Figure 3:
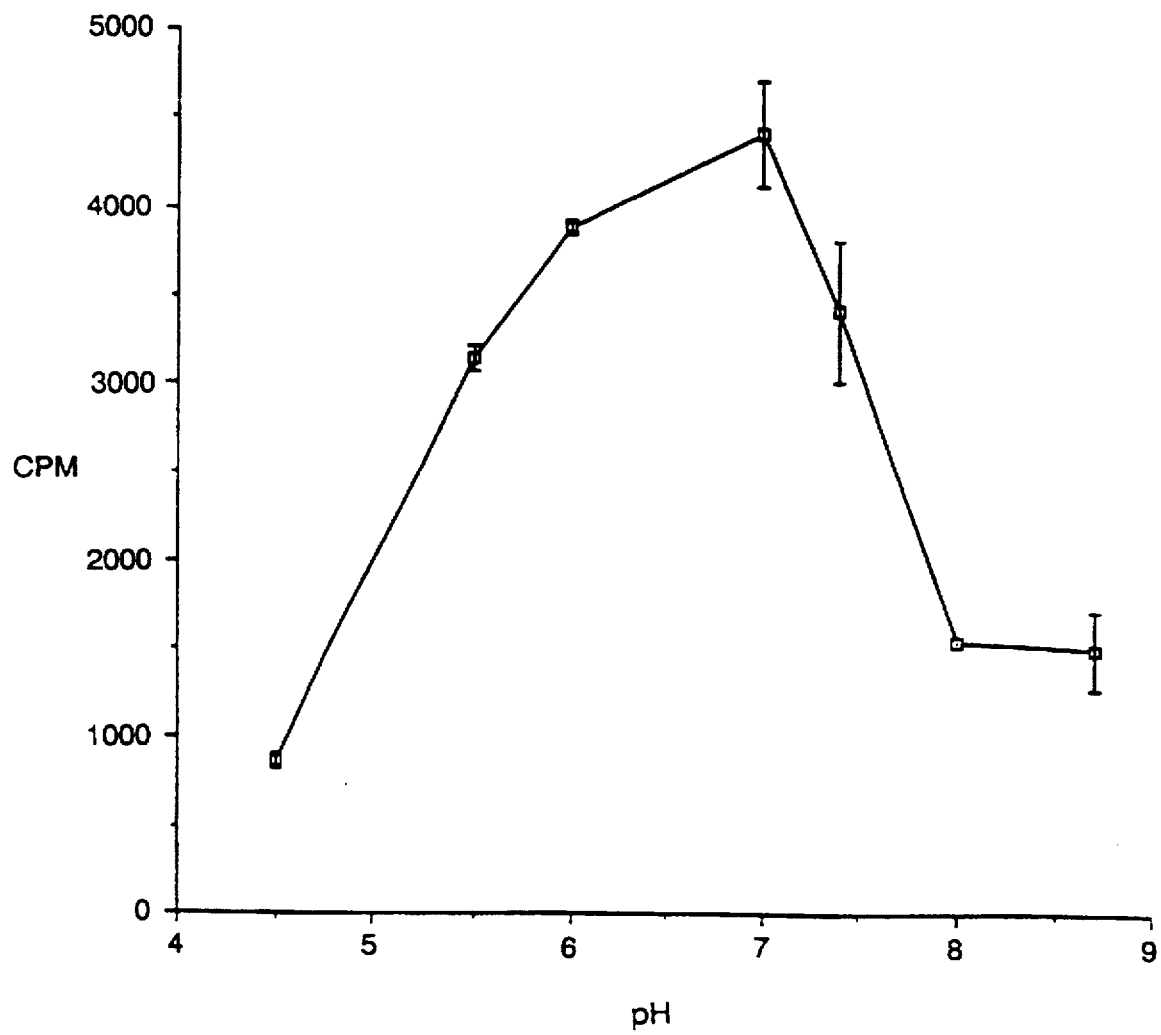
FIG. 3 is a graph depicting the dependence of protease activity on pH. Symbols represent mean values of two determinations and error bars represent the standard deviation from the mean. Error bars not shown are within symbols.
Figure 4:
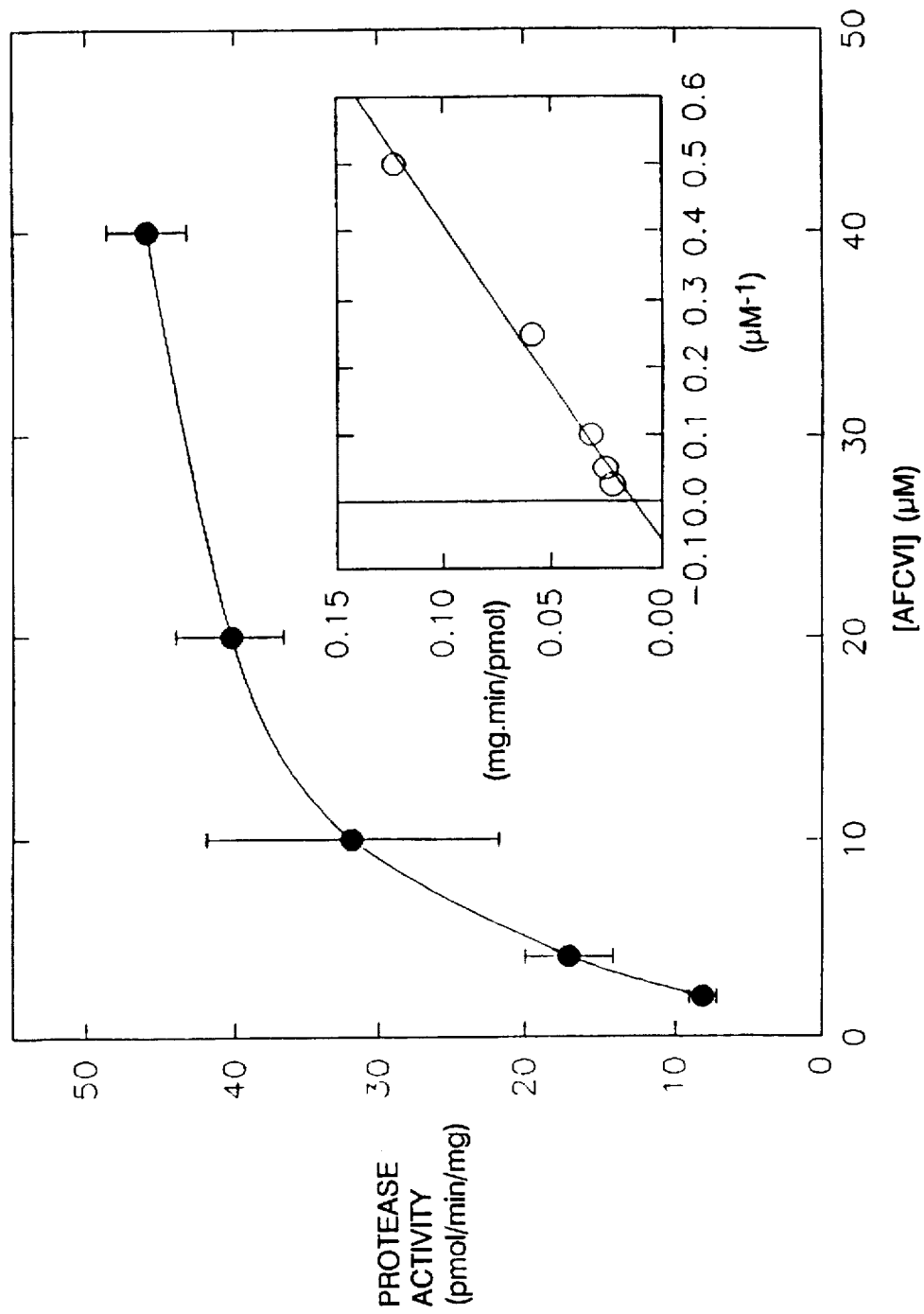
FIG. 4 is a pair of graphs illustrating the kinetics of the formation of N-[$^3$H]-AFC as a function of N-[$^3$H]-Ac-S-farnesyl-L-cys-L-val-L-ile (AFCVI) concentration. Protease activity (pmol/min/mg) is plotted as a function of AFCVI concentration (µM) in panel A. Panel B is an Eadie-Hofstee plot of the same data. Symbols represent mean values of two determinations and error bars represent the standard deviation from the mean. Error bars not shown are within symbols.
Figure 6:
FIG. 6 is a schematic illustration of the synthesis of Boc-S-Farnesyl L-cys and its methyl ester
Figure 7:
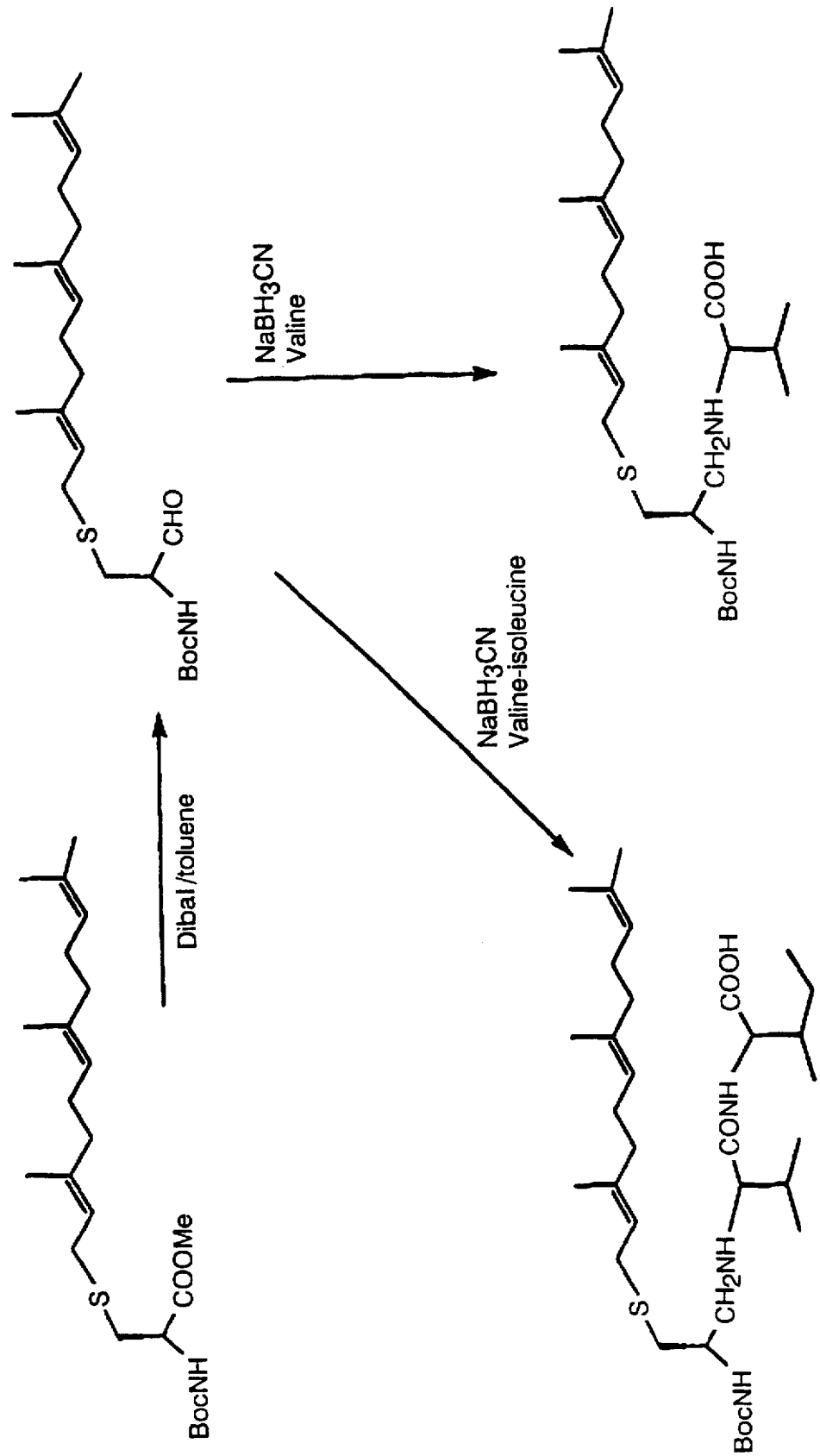
FIGS. 7 and 8, and 9 are schematic illustrations of the synthesis of reduced peptide inhibitors.
Figure 8:
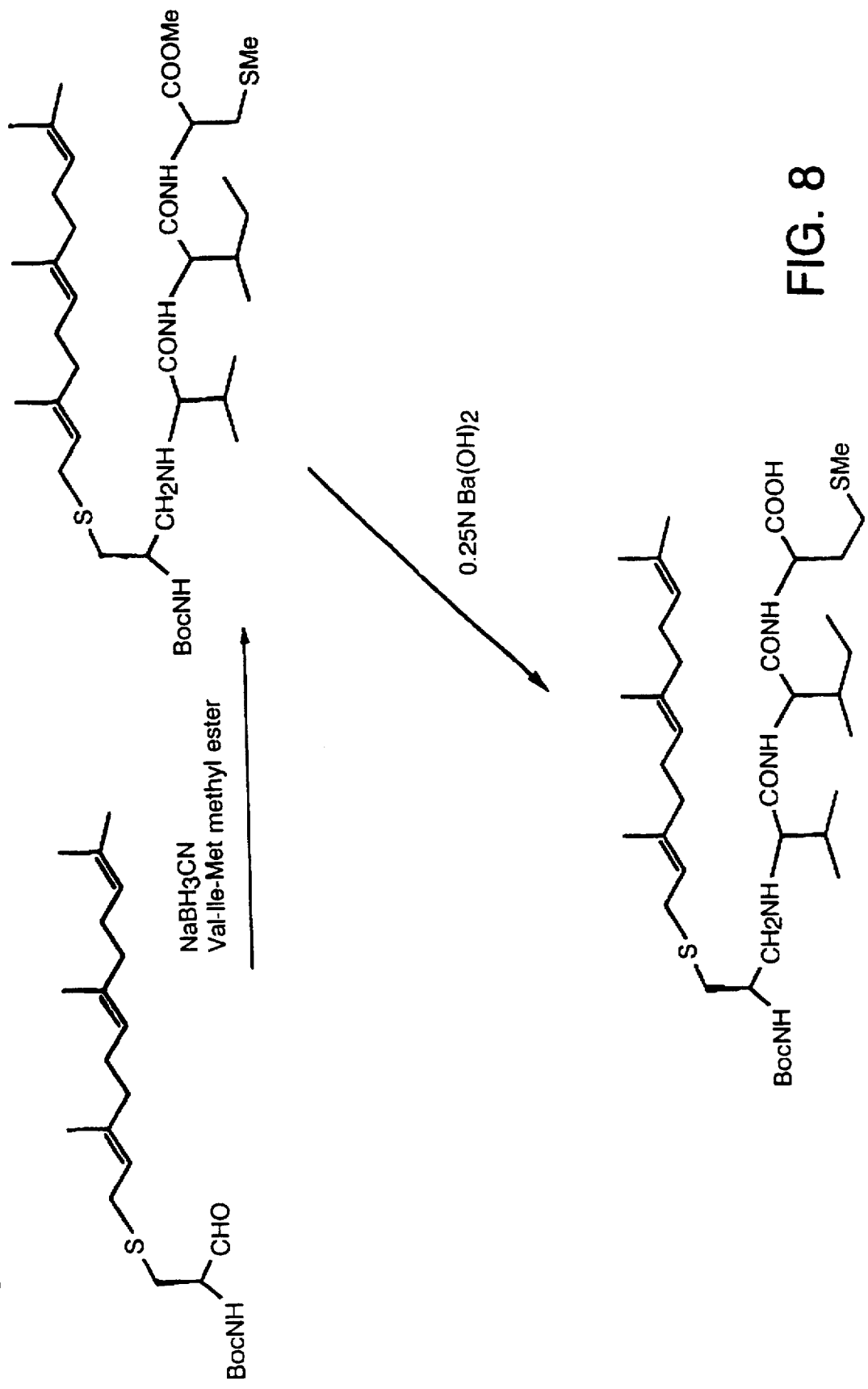
Figure 9:
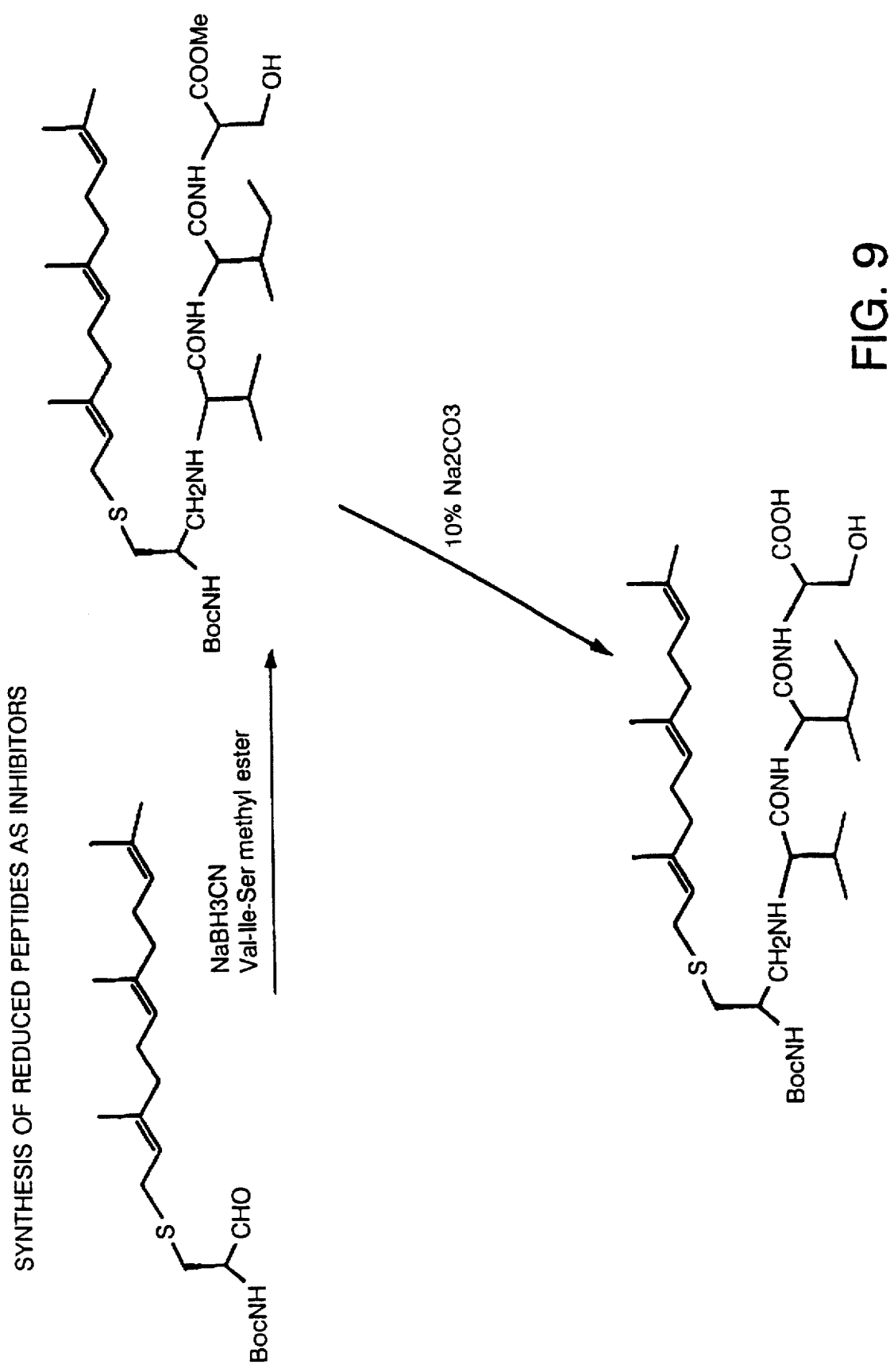
Figure 10:
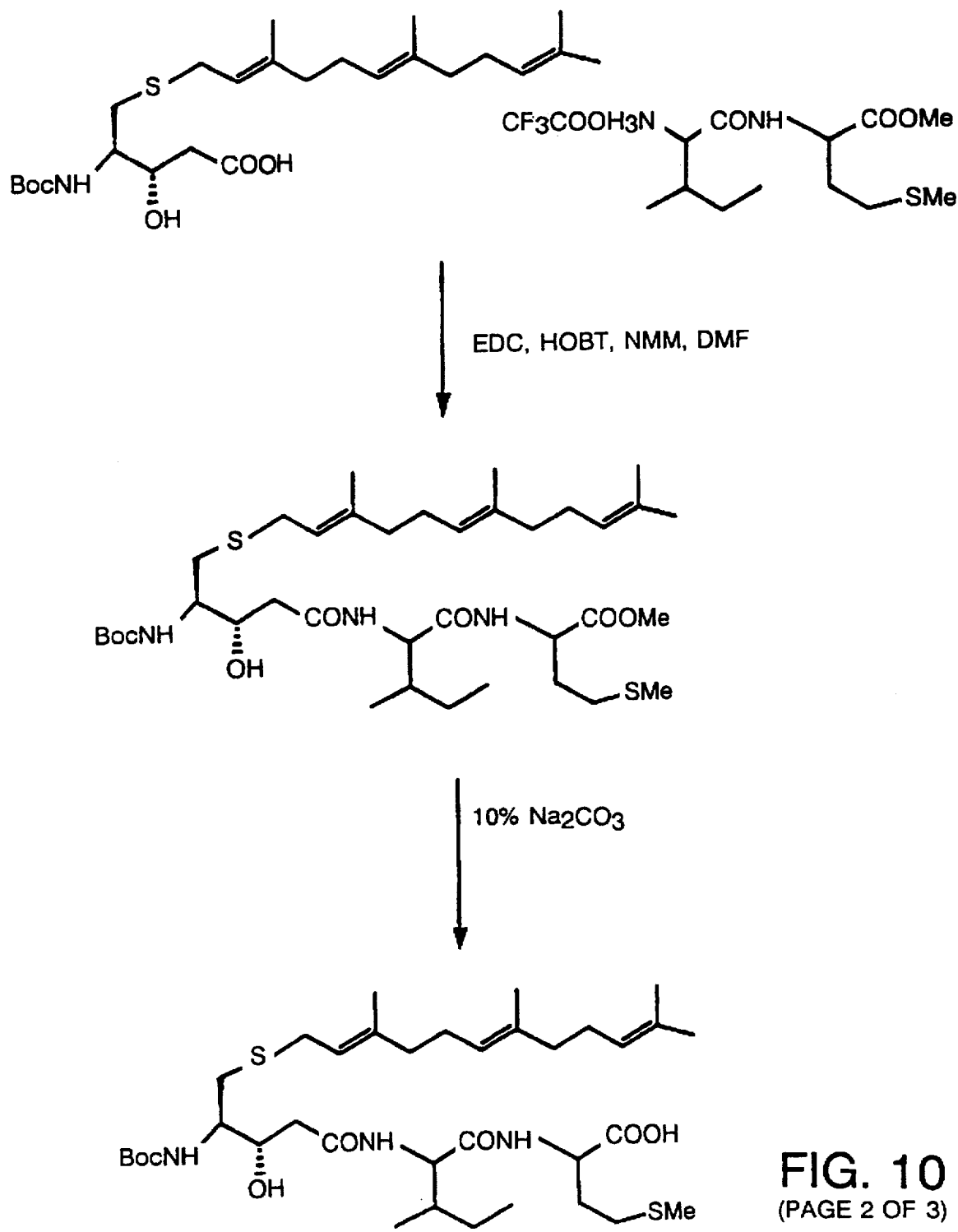
FIG. 10 is a schematic illustration of the synthesis of N-Boc-S-Farnesyl statine derivatives.
Figure 10:
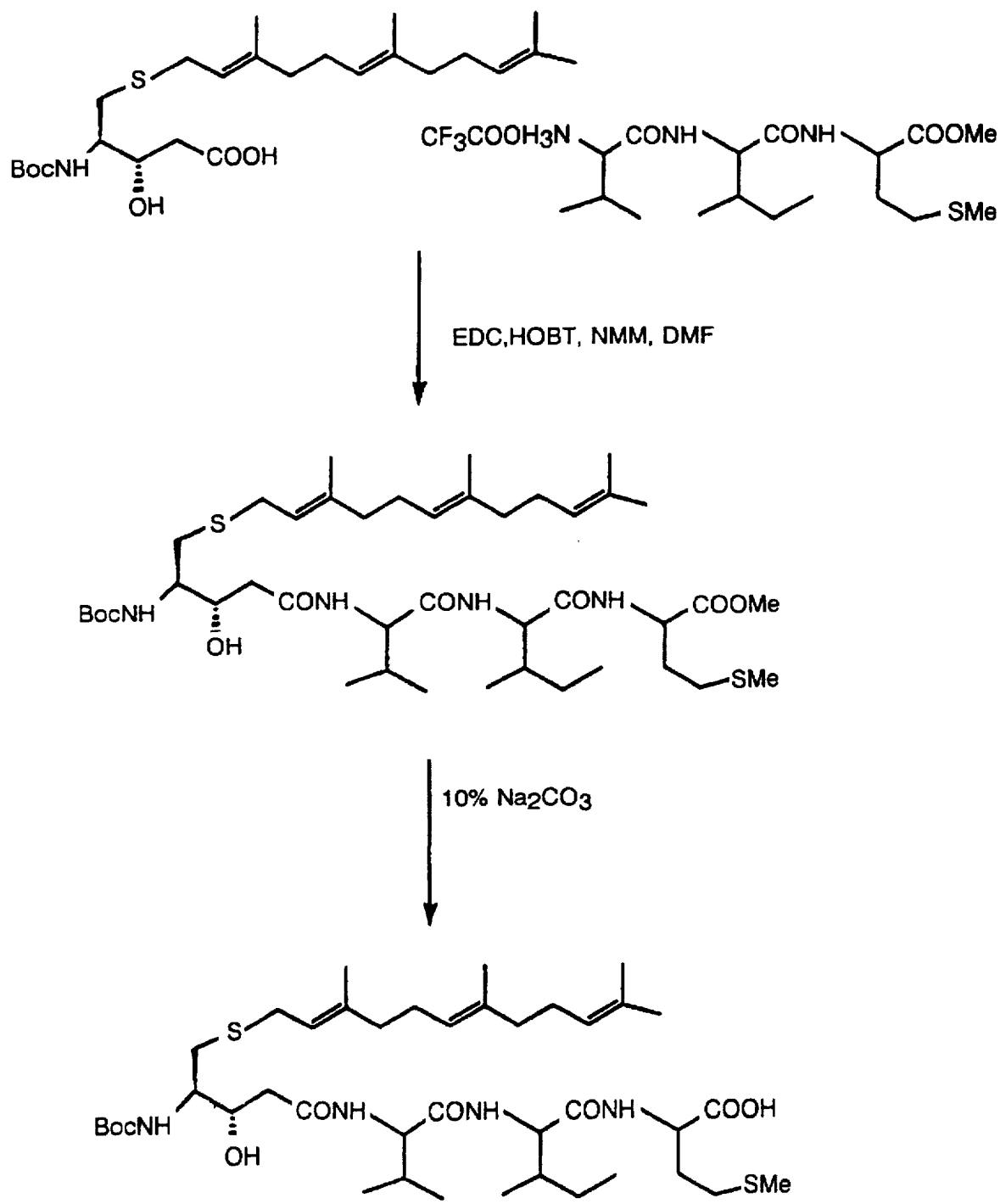

A pH versus rate profile for the proteolysis reaction showed a broad maximum at approximately pH 7. Briefly, the protease activity was determined with 4 µM N-[$^3$H]-Acetyl-S-farnesyl-L-cys-L-val-L-ile-L-ser or N-[$^3$H]acetyl-S-farnesyl-(SEQ ID NO: 1) as substrate in the following buffers: sodium acetate (pH 4.5 and 5.5), sodium phosphate (pH 6.0 and 7.0), Hepes (pH 7.4), and Tris (pH 8.0 and 8.7). Incubation time was 30 minutes. The results of this analysis are presented in FIG. 3.

A similar stereospecific proteolytic enzymatic activity was also found in dog pancreatic microsomes. Under extended incubation conditions, where 54% of the tetrapeptide substrate 1 was cleaved by these microsomes, no proteolysis of D-AFC-val-ile-ser 2 could be detectec. (<1%). Dog pancreas microsomes have already been shown to process farnesylated but unproteolyzed ras protein into the mature protein containing the carboxyl terminal farnesylated cysteine residue (Hancock et al. EMBO J. 10:641, 1991). Synthesis of N-[$^3$H]-acetyl-S-all-trans-farnesyl-L-Cys-L-Val-L-Ile-L-Ser or N-[$^3$H]acetyl-S-farnesyl-(SEQ ID NO: 1)
A solution of N-[$^3$H]-acetyl-S-all-trans-farnesyl-L-Cys-L-

Val-L-Ile (1.12 μmol, 250 mCi/mmol), L-serine hydrochloride methyl ester (20 mg, 0.13 mmol), and 1-hydroxybenzotriazole hydrate (17.4 mg, 0.13 mmol) in 3 mL of DMF was cooled to 0° C. 1-(3-Dimethylamino)propyl-3-ethyl carbodiimide hydrochloride (17.2 mg, 0.09 mmol) and N-methylmorpholine (14.1 μL, 13 mg, 0.13 mmol) were added at 0° C. The mixture was stirred at 0° C. under argon for 2 hours and at room temperature for 24 hours. Water (20 mL) was added and the mixture was extracted with ethyl acetate (4×20 mL). The combined organic layer was washed with 10% HCl, saturated sodium bicarbonate, and water, dried over anhydrous magnesium sulfate, filtered, and evaporated. The residue was dissolved in 3 mL of acetonitrile and 3 mL of 10% aqueous sodium carbonate was added. The mixture was stirred at room temperature for 24 h. 10% HCl was added to adjust the pH to 2. The mixture was then extracted with ethyl acetate (3×20 mL), and the combined organic layer was washed with water, dried over anhydrous magnesium sulfate, filtered, and evaporated. Purification was carried out by HPLC on a Rainin silica 4.6×250-mm column at a flow rate of 1.5 mL/min, using hexane/isopropanol/TFA 85:15:0.1 as eluant. UV detection was at 210 nm. Recovery of radioactivity was 28.2 μCi, $1.13 \times 10^{-4}$ mmol. Retention time was 6.49 min. Data from $^1$H-NMR (500 MHz, DMSO-$d_6$) of the authentic non-radioactive peptide are as follows: δ8.14 (1H,d,J=8 Hz), 7.97 (1H,d,J=7 Hz), 7.86 (1H,d,J=9 Hz), 7.76 (1H,d,J=8.5 Hz), 5.16 (1H, t, J=8.5 Hz), 5.05 (2H,m), 4.48 (1H,brdd,J=6.5, 14 Hz), 4.25 (1H, t, J=8 Hz), 4.20 (1H, brt, J=8 Hz), 4.10 (1H,brd,J=7 Hz), 3.66 (1H,dd, J=6,11 Hz), 3.56 (1H,dd,J=4,11 Hz), 3.08 (2H,m), 2.73 (1H,dd,J=5.5, 13.5 Hz), 2.52 (1H,dd,J=4,11 Hz), 1.90–2.10 (8H,m), 1.84 (3H,s), 1.73 (2H,m), 1.62 (3H,s), 1.60 (3H,s), 1.54 (6H,s), 1.41 (1H,m), 1.30 (1H,m), 0.80 (12H,m).

Synthesis of N-[$^3$H]-acetyl-S-all-trans-farnesyl-D-Cys-L-Val-L-Ile-L-Ser or N-[$^3$H]acetyl-S-farnesyl-(SEQ ID NO: 1) This isomer was prepared by the same method as described above, starting with N-[$^3$H]-acetyl-S-all-trans-farnesyl-D-Cys-L-Val-Ile. The D compound was purified by HPLC. The eluting solvent was hexane/isopropanol/TFA 88:12:0.1 using a Rainen silica column, 4.6×250 mm. Flow rate: 1.5 mL/min with UV detection at 210 nm. Under these conditions, the retention time was 10.7 min. Data from $^1$H-NMR (DMSO-d6, 500 MHz) of the authentic nonradioactive peptide are as follows: δ8.32 (1H,d,J=8 Hz), 8.05 (1H,d,J=7.5 Hz), 7.99 (1H,d,J=10 Hz), 7.95 (1H,d,J=8 Hz), 5.13 (1H,t,J=7 Hz), 5.04 (2H,dt,J=2,7 Hz), 4.59 (1H,dd,J= 8,12 Hz), 4.42 (1H,dd,J=4,9 Hz), 4.24 (2H,m), 3.69 (1-H, dd,J=6,10.5 Hz), 3.60 (1H,dd,5,10.5 Hz), 3.17 (2H,t,J=6.5 Hz), 2.63 (1H,dd,J=8,14 Hz), 2.54 (1H,dd,J=7,14 Hz), 2.06–1.88 (10H,m), 1.81 (3H,s), 1.61 (6H,s), 1.53 (6H,s), 1.22 (1H,m), 1.09 (1H,m), 0.82 (12H,m).

Measurement of Proteolytic Activity Bovine liver microsomes were prepared according to Walter et al. (*Meth. Enzym.* 96:84, 1983). Kinetic measurements were performed by incubating 0.2 mg/mL protein with peptide substrates in 200 mM HEPES buffer containing 100 mM NaCl and 5 mM MgCl$_2$ at pH 7.4, all in a final volume of 50 μL. The peptide substrates were added in DMSO to a final concentration of 4% (v/v) at 37°. The enzymatic reaction was quenched at the appropriate time by the addition of 0.5 mL of chloroform/methanol (1/1, v/v). Phase separation was achieved by adding 0.5 mL 1M citric acid. The chloroform layer was separated and evaporated under nitrogen and the residue was dissolved in n-hexane/2-propanol/TFA containing cold AFC. The formation of the product $^3$H-AFC was followed by HPLC analysis at 210 nm according to Perez-Sala et al. (*Proc. Nat'l Acad. Sci. USA* 88:3043, 1991). The samples were injected onto a normal phase HPLC column (Dynamax 60, Rainin, Woburn, Mass.) connected to a model LB 506-C on-line radioactivity monitor (Berthold, Nashua, N.H.). The column was eluted with n-hexane/2-propanol/TFA [85:15:0.1 (v/v/v)] at 1.5 mL/min.

Synthesis of N-[$^3$H]-acetyl-S-all-trans-farnesyl-L-cys-L-val-L-ile and N-[$^3$H]-acetyl-S-all-trans-farnesyl-D-cys-L-val-L-ile A mixture of S-all-trans-farnesyl-L-Cys-L-Val-L-Ile methyl ester (20 mg, 36 μmol), $^3$H-acetic anhydride (0.02 mmol, ≈10 mCi, 500 mCi/mmol), triethylamine (3.3 μL, 0.024mmol), and a catalytic amount of 4,4-dimethylaminopyridine in 20 mL of methylene chloride was stirred at room temperature overnight. The mixture was filtered and the solvent was evaporated. The residue was separated by HPLC (Rainin silica, 250×4.6 mm, 1.5 mL/min, hexane/isopropanol (85:15), detection at 210 nm, retention time: 4.27 min, yield: 3.57 mCi, 14.28 μmol, 719.) Data from $^1$H-NMR (CDCl$_3$, 500 MHz) of the authentic non-radioactive peptide methyl ester: 6.87 (1H,d,J=8 Hz), 6.47 (1H,d,J=8 Hz), 6.41 (1H,d,J=7 Hz), 5.27 (1H,dt,J=1,7,5 Hz), 5.09 (2H,dt,J=1.5,6 Hz), 4.56 (2H,m), 4.27 (1H,dd,J= 6,8.5 Hz), 3.74 (3H,s), 3.23 (2H,dd,J=1.5,8 Hz), 2.91 (1H, dd,J=6,13.5 Hz), 2.77 (1H,dd,J=7.5,13.5 Hz), 2.22 (1H,m), 2.03 (3H,s), 2.10–1.96 (8H,m), 1.89 (1H,m), 1.67 (6H,s), 1.58 (6H,s), 1.40 (1H,m), 1.18 (1H,m), 0.90 (12H,m).

N-[$^3$H]-acetyl-S-all-trans-farnesyl-L-Cys-L-Val-L-Ile methyl ester (1.19 mCi, 4.76 μmol, 250 mCi/mmol) was dissolved in 12 mL of methanol. KOH/MeOH (5%, 12 mL) was added at 0° C. and the mixture was stirred at 0° C. or 1 h and then at room temperature for 18 h. Basic hydrolysis under these conditions served to specifically racemize the chiral center at the cysteine residue. Acetic acid was added to pH 7. The methanol was evaporated and the residue was extracted with ethyl acetate twice. The combined organic phase was washed with 10% HCl, then with water, then dried over anhydrous sodium sulfate, filtered, and evaporated. Total activity: 1.04 mCi (87%). Purification was carried out by HPLC on Rainin silica 250×4.6 mm column at a flow rate of 1.5 mL/min, using hexane/isopropanol/TFA 92:8:0.01 as eluant. UV detection was at 210 nm. The retention time of the D-L-L isomer was 8.1 min and for the L-L-L isomer it was 10.2 min. Data from $^1$H-NMR (DMSO-d$_6$, 500 MHz) of the authentic non-radioactive peptides: N-Ac-S-all-trans-farnesyl-L-Cys-L-Val-L-Ile: δ8.13 (1H,d, J=8.5 Hz), 7.91 (1H,d,J=8 Hz), 7.79 (1H,d,J=9 Hz), 5.14 (1H,t,J=8 Hz), 5.04 (2H,brs), 4.46 (1H,dd,J=6,10 Hz), 4.25 (1H,dd,J=6,9 Hz), 4.11 (1H,dd,J=6,8 Hz), 3.12 (2H,d,J=7.5 Hz), 2.72 1H,dd,J=6,14 Hz), 2.52 (1H,dd,J=7.5,14 Hz), 2.06–1.89 (9H,m), 1.83 (3H,s), 1.74 (1H,m), 1.61 (3H,s), 1.59 (3H,s), 1.53 (6H,s), 1.38 (1H,m), 1.17 (1H,m), 0.78–0.86 (9H,m). N-Ac-S-all-trans-farnesyl-D-Cys-L-Val-L-Ile : δ8.09 (1H,d,J=8 Hz), 8.07 (1H,d,J=10 Hz), 7.95 (1H,d,J=8 Hz), 5.15 (1H,t,J=8 Hz), 5.04 (2H,t,J=6 Hz), 4.57 (1H,dd,J=6.5,8 Hz), 4.28 (1H,dd,J=7,9 Hz), 4.09 (1H, dd, J=6, 8 Hz), 3.16 (2H,dd,J=4,8 Hz), 2.65 (1H,dd, J=6.5,13.5 Hz), 2.51 (1H,dd,J=7.5, 13.5 Hz), 2.04–1.88 (9H,m), 1.81 (3H,s), 1.75 (1H,m), 1.61 (6H,s), 1.53 (6H,s), 1.40 (1H,m), 1.19 (1H,m), 0.78–0.88 (9H,m)

Specific Enzymatic Cleavage Occurs at the Modified Cysteine Residue

The data described above show that the tetrapeptide 1 is enzymatically processed by microsomal preparations to generate AFC. All studies described 10 below were done with the calf liver microsomal preparation, since it could be obtained readily. It was of special interest to determine where the initial cleavage reaction took place. To accomplish this, the tetrapeptide 1 was synthesized with a tritiated serine 15 residue at the carboxyl terminus (preparation described below). This tetrapeptide was subjected to proteolysis by the microsomal enzyme, and the products were treated with ophthalaldehyde and mercaptoethanol to generate the fluorescently tagged peptides (Trepman et al. *Arch. Biochem. Biophys.* 204:524, 1980).

These peptides could be separated easily on reverse-phase HPLC. This analysis demonstrated that the initial incubation produced virtually only the tripeptide Val-Ile-Ser. Further incubation with the enzyme caused further proteolysis of the tripeptide, to produce the dipeptide. The analysis demonstrated that the initial proteolytic cut is between the AFC moiety and the adjacent valine residue. Further processing of the tripeptide probably occurs by means on nonspecific proteases.

Farnesylated Di- and Tripeptide Substrates of the Protease

The experiments described above demonstrate that the protease is stereospecific at the scissile bond and also requires a free terminal carboxyl group in the tetrapeptide substrate. Substrate specificity was further explored using the tripeptide AFC-val-ile and the dipeptide AFC-val (synthesis described below). The measured $K_M$ and $V_{max}$ values for the tripeptide are 9.2±0.21μM and 58±4.9 pmol/min/mg respectively. The tripeptide is a weaker substrate for the protease than the tetrapeptide. Kinetic constants were not obtained for the dipeptide AFC-val, but it is clearly a substrate for the protease as well. Stereospecificity is also observed with both the dipeptides and tripeptides, because substitution of D-AFC for L-AFC in these molecules led to the complete abolition of substrate activity. Finally, AFC amide is not a substrate for the enzyme, demonstrating that a second amino acid moiety is required, in addition to AFC, in the substrate.

As expected, the proteolysis of [$^3$H]-AFC-val-ile-ser or N-[$^3$H]-(SEQ ID NO: 1) was inhibited by the dipeptide substrate (AFC-val) and by the tripeptide substrate (AFC-val-ile). Incubation of 4 μM substrate along with either 20 μM of the dipeptide or tripeptide led to an approximately 50% diminution in substrate cleavage. Interestingly, deletion of the farnesyl moiety from the tetrapeptide substrate to yield AC-val-ileser did not produce an inhibitor of the enzyme. Incubation of the tetrapeptide substrate with a 5-fold excess of AC-val-ile-ser did not interfere with the processing of the substrate. This result strongly suggests that the isoprenyl moiety is important in enabling the substrate to bind to the enzyme.

A Isoprenoid Moiety Is Important for Substrate Activity

The importance of the isoprenoid Moiety was studied by testing whether the isoprenoid structure affects the ability of various tripeptides to serve as substrates.

For these experiments the substrates were dissolved in DMSC and incubated with calf liver microsomal membranes (0.2 mg of protein/mL) (Walter et al., supra) as described above. The amount of radioactive product was determined as described above. The reaction was quenched with 500 μL of CHCl$_3$/MeOH (1:1, v/v), and the radioactive N-terminal amino acid, i.e. N-[$^3$H]AFC, was extracted after thoroughly agitating this mixture. Phase separation was achieved by adding 500 μL of 1M citric acid. After the chloroform layer was evaporated under nitrogen the residue was resuspended in n-hexane/isopropanol/TFA (90:10:0.01) and non-radioactive AFC was added as a standard for UV detection (210 nm). The sample was injected on a normal-phase HPLC column (Dynamax 60A, Rainin), and elution was performed with the same solvent at flow rate 1.5 ml/min. Radioactivity was counted with an on-line Berthold (Nashua, NH) LB 506-C HPLC radioactivity monitor. The limit of efficiency of this assay was 3× the background counts/min (~150 cpm), which permits detection of products from substrates whose activities are 0.4% of the $V_{max}$ of AFC-Val-Ile-Ser (SEQ ID NO: 1) (1.13 pmol/min/mg). The retention times for AGC, AFC, and AGGC are 7.58, 7.26, and 7.00 min respectively, and for AGC-Val-Ile, AFC-Val-Ile, and AGGC-Val-Ile, they are 5.48, 6.54, and 5.08 min respectively.

Because the experiments described above demonstrate that acetyl-S-all-trans-farnesyl-L-Cys-Val-Ile (AFC-Val-Ile) can serve as a substrate for the protease, the all-trans-geranyl-geranyl derivative (AGCCC-Val-Ile) and the all-trans-geranyl derivative (AGC-Val-Ile) were prepared and tested. Both analogs were good substrates for the protease.

The geranylgeranyl derivative was hydrolyzed with a $K_M$ was 14.6 μM and the Vmax was 19.35 pmol/min/mg respectively (Table 1). As expected, stereospecificity was observed with respect to the isoprenylated amino acid, because no measurable protease activity was observed with neither D-AGGC-Val-Ile or D-AGC-Val-Ile as a substate (Table 1).

The experiments described above demonstrate that the protease exhibits a broad substrate specificity profile with respect to isoprenoid side chains. To resolve is whether or not the isoprenoid side-chain is essential, the following non-isoprenylated were prepared and studied: the cysteine analog C-V-I and the t-butylthio derivative of C-V-I. Neither analog was measurably processed by cleavage between the cysteine and valine residues (Table 1). These experiments demonstrate than an isoprenoid moiety is important for activity.

Sterospecificity Requirements of Substrates

Various stereoisomers of AFC-Val-Ile were prepared and tested for their ability to serve as a substrate for the protease.

The L-D-L and L-L-D analogs did not have substrate activity (Table 1). The same specificity was observed for the AFC-val-ile-ser (SEQ ID NO: 1) series. Further, all analogs studied in the AFC-val-ile series in which there was more than one D amino acid (e.g. D-D-D, D-D-L, D-L-D and L-D-D) were inactive. The stereospecificity at the X position of -CAAX was explored using L-AFC-Val-Ile-D-Met (SEQ ID NO: 2) and L-AFC-Val-Ile-L-Met (SEQ ID NO: 2). As shown in Table 1, only the all L tetrapeptide proved to be a good substrate for the enzyme. However, the L-L-L-D derivative proved to be processed to some extent, although the minimal amount of product formed precluded kinetic analysis. These data taken together show that the protease is stereospecific with respect to the CAA moieties, and stereoselective with respect to X.

TABLE 1

| SUBSTRATE (pmol/min/mg) | ISOMER | $K_M$ (μM) | max V |
|---|---|---|---|
| AFC-Val-Ile (1) | L-L-L | 9.2 ± 0.2 | 57.7 ± 5 |
| AGGC-Val-Ile (2) | L-L-L | 4.01 ± 0.4 | |
| 26.20 ± 0.97 | D-L-L | | inactive* |
| AGC-Val-Ile (3) | L-L-L | 14.60 ± 2.14 | |
| 19.35 ± 1.12 | D-L-L | | inactive* |
| Cys-Val-Ile (4) | L-L-L | | inactive* |
| t-butylthio-Cys-Val-Ile (5) | L-L-L | | inactive* |
| AFC-Val-Ile (6) | D-L-L | | inactive* |
| AFC-Val-Ile (7) | L-D-L | | inactive* |
| AFC-Val-Ile (8) | L-L-D | | inactive* |
| AFC-Val-Ile-Met (9) | L-L-L-L | 2.96 +/− 0.35 | 126.3+/− 4.7 |
| AFC-Val-Ile-Met (10) | L-L-L-D | | weakly active** |

Values given are average values of two determinations ±S.D. We had previously measured 1 to have $K_M$ and $V_{max}$ values of 12.6 μM and 65.6 pmol/min/mg. These values are slightly lower than those reported here. However, the former measurement was performed on a different microsome preparation from a different animal. The measurements reported in this table were all determined using the same enzyme preparation. *Analogs referred to as inactive did not show detectable activity as substrate when used at concentration of 10mM and prolonged incubation time (16 hours). The sensitivity of START HERE the assay used allows the detection of protease activities above 1.13 pmol/min/mg (0.4% of the activity seen with AFC-V-I-S (SEQ ID NO: 2)). **Where marginal activity is noted, detectable activity is observed under prolonged incubation periods, but the activity is <5% that observer, with AFC-V-I-S.

Synthesis of N-[$^3$H]-Acetyl-S-trans-geranyl-L-Cys-L-Val-L-Ile and N-[$^3$H]-Acetyl-S-trans-geranyl-D-Cys-L-Val-L-Ile A mixture of S-trans-geranyl-L-cys-L-val-L-ile methyl ester (20 mg, 41 μmol), [$^3$H]-acetic anhydride (6 μmol, 3 mCi, 500 mCi/mmol), and a catalytic amount of 4,4-dimethylaminopyridine in 6 mL of methylene chloride as stirred at room temperature overnight. The mixture was filtered and the solvent was evaporated. The residue was purified by HPLC (Rainin silica, 250×4.6 μm, 1.5 mL/min, hexane/isopropanol 85:15, uv detection was at 210 nm). Retention time: 4.13 min. Yield: 1.079 mCi, 4.32 μmol, 72%.

$^1$HNMR (CDCl$_3$, 500 MHz) of the authentic non-radioactive peptide methyl ester: 6.88 (1H,d,J=8 Hz), 6.50 (1H,d,J=9 Hz), 6.43 (1H,d,J=7.5 Hz), 5.26 (1H,t,J=7 Hz), 5.06 (1H,t,J=7 Hz), 4.56 (2H,m), 4.28 (1H,dd,J=6.5,8.5 Hz), 3.72 (3H,s), 3.23 (2H,dd,J=2,8 Hz), 2.91 (1H,dd,J=5,13.5 Hz), 2.77 (1H,dd,J=8,13.5 Hz), 2.21 (1H,m), 2.04 (3H,s), 2.08–2.02 (4H,m), 1.90 (1H,m), 1.68 (3H,s), 1.67 (3H,s), 1.59 (3H,s), 1.41 (1H,m), 1.18 (1H,m), 0.88–0.96 (12H,m).

A suspension of N-[$^3$H]-acetyl-S-trans-geranyl-L-cysteine-L-valine-L-isoleucine methyl ester (1.079 mCi, 4.32kimol,250mCi/mmol) and 0.25M barium hydroxide in methanol-water(1:1.5mL) was stirred at room temperature for 2 days. 10% HCl was added to pH=2. The mixture war; extracted with ethyl acetate (3×30 mL). The combined organic phase was washed with water, dried over anhydrous magnesium sulfate, filtered, and evaporated. The residue was separated by HPLC (Rainin silica, 250×4.6 mm, 1.5 mL/min, hexane/isopropanol/TFA 92:8:0.01, UV detection was at 210 nm). The retention time of the D-L-L isomer was 7.17 min. and for the L-L-L isomer it was 9.65 min. Recovery of radioactivity:D-L-L:0.22 mCi, L-L-L:0.18 mCi. $^1$HNMR(DMSO-d$_6$, 500 MHz) of the authentic non-radioactive peptides:

N-acetyl-S-trans-geranyl-L-Cys-L-Val-L-Ile: 8.11 (1H,d, J=8 Hz), 7.89 (1H,d,J=8 Hz), 7.76 (1H,d,J=8.5 Hz), 5.15 (1H,t,J=8 Hz), 5.03 (1H,t,J=6.5 Hz),4.46 (1H,dd,J=8.5,9 Hz), 4.25 (1H,dd,J=7,9 Hz), 4.12 (1H,dd,J=6,8 Hz), 3.13 (2H,t,J=9 Hz), 2.72 (1H,dd,J=6,14 Hz), 2.53 (1H,dd,J=9, 14 Hz), 1.94–2.08 (5H,m), 1.96 (1H,m), 1.83 (3H,s), 1.61 (3H,s), 1.59 (3H,s), 1.54 (3H,s), 1.40 (1H,m), 1.18 (1H, m), 0.78–0.88 (12H,m).

N-acetyl-S-trans-geranyl-D-Cys-L-Val-Ile: 8.07 (1H,d,J=7 Hz), 8.04 (1H,d,J=9 Hz), 7.93 (1H,d,J=7.5 Hz), 5.15 (1H,t,J=7 Hz), 5.03 (1H,t,J=6.5 Hz), 4.56 (1H,dd,J=8,14.5 Hz), 4.28 (1H,dd,J=7,9 Hz), 4.10 (1H,dd,J=5.5,7.5 Hz), 3.16 (2H,dd,J=2,8 Hz), 2.67 (1H,dd,J=7,13.5 Hz), 2.53 (1H,dd,J=7.5,13.5 Hz), 1.96–2.05 (5H,m), 1.96 (1H,m), 1.82 (3H,s), 1.61 (3H,s), 1.60 (3H,s), 1.54 (3H,s), 1.41 (1H,m), 1.18 (1H,m), 0.80–0.86 (13H,m).

synthesis of N-[$^3$H]-Acetyl-S-all-trans-geranylgeranyl-L-Cys-L-Val-L-Ile and N-[$^3$H]-Acetyl-S-all-trans-geranylgeranyl-D-cys-L-Val-L-Ile A mixture of S-all-trans-geranylgeranyl-L-cys-L-Val-L-Val-Ile methyl ester (20 mg, 32 μmol), [$^3$H]-acetic anhydride (μmol, 2.5 mCi, 500 mCi/mmol), and a catalytic amount of 4,4-dimethylaminopyridine in 4 mL of methylene chlroride was stirred at room temperature overnight. The solvent was evaporated and the residue was partitioned between water and ethyl acetate. The aqueous layer was extracted with ethyl acetate (2×30 mL). The combined organic phase was washed with 10% HCl, saturated sodium bicarbonate, and water, dried over anhydrous magnesium sulfate, filtered, and evaporated. The residue was purified by HPLC (Rainin silica, 250×4.6 mm, 1.5 mL/min, hexane/isopropanol/TFA 90:10:0.01, uv detection was 210 nm). Retention time: 4.70 min. Yield: 0.40 mCi, 1.6 μmol, 32%.

$^1$HNMR (CDCl$_3$, 500 MHz) of the authentic non-radioactive peptide methyl ester: 6.92 (1H,d,J=9 Hz), 6.57 (1H,d,J=8.5 Hz), 6.47 (1H,d,J=7 Hz), 5.26 (1H,t,J=8 Hz), 5.09 (3H,t,J=5 Hz), 4.57 (2H,m), 4.30 (1H,dd,J=6,8 Hz), 3.76 (3H,s), 3.22 (2H,dd,J=2.7 Hz), 2.90 (1H,dd,J=5,13.5 Hz), 2.77 (1H,dd,J=7.5,J=7,14 Hz), 3.16 (2H,d,J=8 Hz), 2.66 (1H,dd,J=5,12.5 Hz), 2.52 (1H,dd,J=7.5,12.5 Hz), 1.96–2.08 (13H,m), 1.81 (3H,s), 1.78 (1H,m), 1.61 (6H,s), 1.54 (9H,s), 1.42 (1H,m), 1.18 (1H,m), 0.78–0.86 (12H,m).

Syntheses of N-[$^3$H]-acetyl-S-all-trans-farnesyl-L-cys-D-Val-L-Ile and N-[$^3$H]-acetyl-S-all-trans-farsenyl-D-Cys-D-Val-L-Ile A solution of N-[$^3$H]-acetyl-S-all-trans-farnesyl-cysteine (0.31 mCi, 124 μmol, 250 mCi/mmol, prepared by acetylation of all-trans-farnesyl-L-cysteine), D-valine-L-isoleucine p-nitrobenzyl ester tosylate (40.6 mg, 76 μmol), and 1-hydroxybenzotriazole hydrate (12 mg, 89 μmol) in 6 mL of DMF was cooled to 0° C. N-methylmorpholine (10 mL, 9.2 mg, 91 μmol) and 1-(3-dimethylamino)propyl-3-ethyl carbodiimide hydrochloride (15.2 mg, 80 μmol) were added at 0° C. The mixture was stirred under argon at 0° C. for 2 hours and at room temperature for 22 hours. Water (20 mL) was added and the mixture was extracted with ethyl acetate (3×30 mL). The combined organic phase was washed with 10% HCl, saturated sodium bicarbonate, water, dried over anhydrous magnesium sulfate, filtered, and evaporated. The residue was redissolved in 8 ml of 90% aqueous acetic acid. Zinc dust (500 mg) was added and the mixture was stirred at room temperature for 29 hours. Ethyl acetate (30 mL) was added and the aqueous layer was extracted with ethyl acetate (2×30 mL). The combined organic phase was washed with water, dried over anhydrous magnesium sulfate, filtered, and evaporated. The residue was separated by HPLC (Rainin silica, 4.6×250 mm, hexane/isopropanol/TFA 92:8:0.01, 1.5 mL/min, UV detection was at 210 nm). The recovery of radioactivity was 0.19 mCi for the L-D-L isomer and 0.08 mCi for the D-D-L isomer. The HPLC retention times for the L-D-L and D-D-L isomers were 8.60 min and 6.26 min respectively. $^1$HNMR (DMSO-d$_6$, 500 MHz) of authentic non-radioactive peptides:

N-acetyl-S-all-trans-farnesyl-L-Cys-D-Val-L-Ile 8.11 (1H, d,J=9.5 Hz), 8.09 (1H,d,J=7.5 Hz), 8.01 (1H,d,J=7.5 Hz), 5.15 (1H,t,J=8 Hz), 5.04 (2H,t,J=8 Hz), 4.59 (1H,dd,J=8, 15 Hz), 4.34 (1H,dd,J=6,9 Hz), 4.18 (1H,dd,J=6.5,8.5 Hz), 3.17 (2H,dd,J=4,7.5 Hz),2.65 (1H,dd,J=6.5,13.5 Hz), 2.51 (1H,dd,J=7.5,13.5 Hz), 2.08–1.90 (9H,m), 1.80 (3H, s), 1.79 (1H,m,) 1.61 (3H,s), 1.60 (3H,s), 1.54 (6H,s), 1.38 (1H,m), 1.19 (1H,m), 0.79–0.87 (12H,m).

N-acetyl-S-all-trans-farnesyl-D-Cys-D-Val-L-Ile 8.19 (1H, d,J=8.5 Hz), 7.89 (1H,brs), 7.77 (1H,d,J=8.5 Hz), 5.14 (1H,t,J=8 Hz), 5.04 (2H,t,J=6 Hz), 4.46 (1H,dd,J=7,9 Hz), 4.26 (1H,dd,J=6,13 Hz), 4.15 (1H,brs), 3.15 (1H,d,J= 8Hz), 3.12 (1H,d,J=Hz)2.73 (1H,dd,J=5.5,12.5 Hz), 2.51

(1H,dd,J=8.5,12.5 Hz), 2.06–1.90 (9H,m), 1.83 (3H,s), 1.78 (1H,m), 1.61 (3H,s), 1.60 (3H,s), 1.53 (6H,s), 1.39 (1H,m), 1.18 (1H,m), 0.79–0.84 (12H,m).

Synthesis of N-[$^3$H]-acetyl-S-all-trans-farnesyl-L-Cys-L-Val-D-Ile 1-(3-Dimethylamino)propyl-3-ethyl carbodiimide hydrochloride (15.2 mg, 80 μmol) were added to a stirred solution of N-[$^3$H]-acetyl-S-all-trans-farnesyl-cysteine (0.31 mCi, 1.24 μmol, 250 mCi/mmol, prepared by acetylation of all-trans-farnesyl-L-cysteine), L-valine-D-isoleucine p-nitrobenzyl ester tosylate (40.6 mg, 76 μmol), 1-hydroxybenzotriazole hydrate (12 mg, 89 μmol), and N-methylmorpholine (10 μL, 9.2 mg, 91 μmol) in 6 mL of DMF at 0° C. The mixture was stirred under argon at 0° C. for 2 hours and at room temperature for 22 hours.

Water (20 mL) was added and the mixture was extracted with ethyl acetate (3×30 mL). The combined organic phase was washed with 10% HCl, saturated sodium bicarbonate, water, dried over anhydrous magnesium sulfate, filtered, and evaporated. The residue was redissolved in 8 mL of 90% aqueous acetic acid. Zinc dust (500 mg) was added and the mixture was stirred at room temperature for 25 hours. The aqueous mixture was extracted with ethyl acetate (3×30 mL). The combined organic phase was washed with water, dried over anhydrous magnesium sulfate, filtered, and evaporated. The residue was separated by HPLC (Rainin silica, 4.6×250 mm, hexane/isopropanol/TFA 92:8:0.01, 1.5 mL/min, UV detection was at 210 nm). The recovery of radioactivity was 0.21 mCi for the L-L-D isomer and 0.07 mCi for the D-L-D isomer. The HPLC retention times for the L-L-D and D-L-D isomers were 8.19 min and 6.42 min respectively. $^1$HNMR (DMSO-d$_6$, 500 MHz) of authentic non-radioactive peptides: L-L-D is same as D-D-L above. D-L-D is same as L-D-L above.

Synthesis of N-[$^3$H]-Acetyl-S-thio-t-butyl-L-Cys-L-Val-L-Ile:

A mixture of S-thio-t-butyl-L-Cys-L-Val-L-Ile (5 mg, 11.9 μmol), 16.6 mL of ten times diluted triethylamine with anhydrous methylene chloride (1.1 eqv) 30 and 3.2mL [$^3$H]-acetic anhydride (4 mmol, 2 mCi, 500 mCi/mmol) in 3.3 mL methylene chloride solution and stirred overnight at room temperature under argon. The mixture was evaporated and the product was separated from the unreacted starting material by reverse phase HPLC on a Dynamax (Rainin), C-18, particle size: 8 μ, pore size: 60 Å, column size: 10×250 mm. The mobil phase was 10 mM TFA in 1:1 acetonitrile/water and the flow rate was 2.0 mL/min. with detection at 210nm. The retention time of the product was 14.75min. and the yield was 94%.

$^1$H NMR (DMSO-d$_6$, 500 MHz): 8.24 (1H,d,J=8.0 Hz), 7.93 (1H,d,J=7.5 Hz), 7.83 (1H,d,J=80 Hz), 4.53 (1H,ddd, J=3.5,8.5,11.5 Hz), 4.23 (1H,dd,J=8.5,8.5 Hz), 4.11 (1H,dd, J=6.0,8.0 Hz), 3.03 (1H,dd,J=4.5,12.5 Hz), 2.88 (1H,dd,J= 9,12.5 Hz), 1.95 (1H,m), 1.84 (3H,s), 1.35 (1H,m), 1.26 (9H,s), 1.26–1.17 (2H,m), 0.84–0.76 (12H,m).

Synthesis of N-[$^3$H]-Acetyl-L-Cys-L-Val-L-Ile:

N-[$^3$H]-Acetyl-S-thio-t-butyl-L-Cys-L-Val-L-Ile (0.25 mCi, 250 mCi/mmol, 1 mmol) was stirred with a 10-fold excess of tributyl phosphine in 500 μL of 20% aqueous n-propanol (w/w) under argon at room temperature for 48h. The reaction mixture was then freeze-dried and the product was purified from the residue by reverse phase HPLC as described above. The purified compound gave positive DTNB test for free sulfhydryl group and had a retention time of 7.27 min. The yield of purified material was 15%.

N-[$^3$H]-acetyl-S-all-trans-farnesyl-L-Cys-L-Val-L-Ile-D-Met methyl ester

A mixture of S-all-trans-farnesyl-L-cysteine-L-valine-L-isoleucine-D-methionine methyl ester (20 mg, 26 μmol), [$^3$H]-acetic anhydride (4μmol, 2mCi, 500 mCi/mmol), and a catalytic amount of 4,4-dimethylaminopyridine in 3.2 mL of methylene chloride was stirred at room temperature overnight. Water was added and the mixture was extracted with ethyl acetate three times. The combined organic phase was washed with 10% HCl, saturated sodium bicarbonate, water, dried over anhydrous magnesium sulfate, filtered, and evaporated. The residue was purified by HPLC (Rainin silica, 250×4.6mm, 1.5mL/min, hexane/isopropanol 85:15, uv detection was at 210nm). Retention time: 5.15 min. Yield: 0.134 mCi, 0.54 μmol, 13.4%.

$^1$HNMR (CDCl$_3$, 500 MHz) of the authentic nonradioactive peptide methyl ester: 6.96 (2H,brs), 6.58 (2H,brs) 5.25 (1H,t,J=7 Hz), 5.09 (2H,t,J=6 Hz), 4.72–4.62 (2H,m), 4.44 (1H,dd,J=6,12 Hz), 4.08 (1H,t,J=8 Hz), 3.76 (3H,s), 3.25 (2H,t,J=8 Hz), 2.93 (1H,dd,J=5,14 Hz), 2.83 (1H,dd,J=8,14 Hz), 2.54 (2H,m), 2.30 (1H,m), 2.18–2.04 (9H,m), 2.08 (3H,s), 2.04 (3H,s), 1.97 (2H,m), 1.69 (3H,s), 1.68 (3H,s), 1.58 (6H,s), 1.44 (1H,m), 1.10 (1H,m), 0.93 (12H,m).

N-[$^3$H]-acetyl-S-all-trans-farnesyl-L-Cys-L-Val-L-Ile-D-Met

A solution of N-[$^3$H]-acetyl-S-all-trans-farnesyl-L-cysteine-L-valine-L-isoleucine-D-methionine methyl ester (0.134 mCi, 0.54μmol, 250 mCi/mmol) and 10% sodium carbonate (10 mL) in acetonitrile (10 mL) was stirred at room temperature of 36 hours. 10% HCl was added to pH=2. The mixture was extracted with ethyl acetate (3×30 mL). The combined organic phase was washed with water, dried over anhydrous magnesium sulfate, filtered, and evaporated. The residue was separated by HPLC (Rainin silica, 250× 4.6mm, 1.5mL/min, hexane/isopropanol/TFA 90:10:0.01, UV detection was at 210nm). The retention time was 9.38 min. Recovery of radioactivity: 0.094 mCi, 70%.

$^1$HNMR (DMSO-d$_6$, 500 MHz) of the authentic non-radioactive peptide: 8.15 (1H,d,J=8 Hz), 8.13 (1H,d,J=8.5 Hz), 7.86 (1H,d,J=9 Hz), 7.75 (1H,d,J=8.5 Hz), 5.15 (1H,t, J=Hz), 5.04 (2H,d,J=3.5 Hz), 4.46 (1H,dd,J=8,14 Hz), 4.28–4.16 (3H,m), 3.13 (2H,d,J=7.5 Hz), 2.71 (1H,dd,J=6, 14 Hz), 2.51 (1H,dd,J=8.5,14 Hz), 2.46–2.39 (3H,m), 1.99 (3H,s), 2.03–1.90 (10H,m), 1.82 (3H,s), 1.68 (1H,m), 1.61 (3H,s), 1.59 (3H,s), 1.53 (6H,s), 1.39 (1H,m), 1.03 (1H,m), 0.78 (12H,m).

N-[$^3$H]-acetyl-S-all-trans-farnesyl-L-Cys-L-Val-L-Ile-L-Met or N-[$^3$H]acetyl-S-all-trans-farnesyl-L-(SEQ ID NO: 2) methyl ester A mixture of S-all-trans-farnesyl-L-cysteine-L-valine-L-isoleucine-L-methionine or S-all-trans-farnesyl-L-(SEQ ID NO: 2) methyl ester (20 mg, 26 μmol), [$^3$H]-acetic anhydride (10μmol, 5 mCi, 500 mCi/mmol, and a catalytic amount of 4,4–10 dimethylaminopyridine in 8 ml of methylene chloride was stirred at room temperature overnight. Water was added and the mixture was extracted with ethyl acetate three times. The combined organic phase was washed with 10% HCl, saturated sodium bicarbonate, water, dried over anhydrous magnesium sulfate, filtered, and evaporated. The residue was purified by HPLC (Rainin silica, 250×4.6mm, 1.5mL/min, hexane/isopropanol 85:15, uv detection was at 210 nm). Retention time: 4.26 min. Yield: 0.588 Ci, 2.5 μmol, 12%.

$^1$HNMR (DMSO-d$_6$, 500 MHz) of the authentic non-radioactive peptide methyl ester:8.31 (1H,d,J=6.5 Hz), 8.13 (1H,d,J=8 Hz), 7.81 (2H,d,J=8.5 Hz), 5.15 (1H,t,J=8 Hz), 5.04 (2H,m), 4.45 (1H,ddd,J=2,9,14.5 Hz), 4.36 (1H,ddd,J= 2,5,9.5 Hz), 4.18 (1H,dd,J=6.5,8.5 Hz), 4.15 (1H,t,J=9 Hz), 3.13 (2H,d,J=7.5 Hz), 2.71 (1H,dd,J=6,13.5 Hz), 2.50 (1H, dd,J=8,13.5 Hz), 2.49 (1H,m), 2.41 (1H,m), 2.03–1.89 (10H, m), 2.00 (3H,s), 1.82 (3H,s), 1.68 (1H,m), 1.61 (3H,s), 1.59 (3H,s), 1.53 (6H,s), 1.41 (1H,m), 1.05 (1H,m), 0.79 (12H, m).

N-[$^3$H]-acetyl-S-all-trans-farnesyl-L-cys-L-Val-L-Ile-L-Met

A solution of N-[$^3$H]-acetyl-S-all-trans-farnesyl-L-cysteine-L-valine-L-isoleucine-L-methionine methyl ester (0.588 mCi, 2.35mmol, 250μmmol, 250 μCi/mmol) and 10% sodium carbonate (10 mL) in acetonitrile (10 mL) was stirred at room temperature for 36 hours. 10% HCl was added to pH=2. The mixture was extracted with ethyl acetate (3×30 mL). The combined organic phase was washed with water, dried over anhydrous magnesium sulfate, filtered, and evaporated. The residue was separated by HPLC (Rainin silica, 250×4.6 mm, 1.5 mL/min, hexane/isopropanol/TFA 90:10:0.01, uv detection was at 210 nm). The retention time was 6.68 min. Recovery of radioactivity:0.29 mCi, 49%.

$^1$HNMR (DMSO-d$_6$,500 MHz) of the authentic non-radioactive peptide: 8.14 (1H,d,J=8 Hz), 8.12 (1H,d,J=8 Hz), 7.85 (1H,d,J=8.5 Hz), 7.81 (1H,d,J=9.5 Hz), 5.15 (1H,t,J=8 Hz), 5.05 (2H,m), 4.46 (1H,ddd,J=2,6, 14.5 Hz), 4.39 (1H,dd,J=5,5,9.5 Hz), 4.33 (1H,ddd,J=5,10,14 Hz), 4.23 (1H,dd,J=7,8.5 Hz), 3.17 (1H,dd,J=8,14 Hz), 3.12 (1H,dd,J=7.5,14 Hz), 2.74 (1H,dd,J=6,13.5 Hz), 2.52 (1H, dd,J=7.5,13.5 Hz), 2.46–2.35 (3H,m), 2.00 (3H,s), 2.04-1.90 (10H,m) 1.83 (3H,s), 1.61 (3H,s), 1.60 (3H,s), 1.53 (6H,s), 1.24 (2H,m), 1.08 (1H,m), 0.80 (12H,m).

Design and Screening of Inhibitors

The structure/activity studies described above suggest that the isoprenylated cysteine residue is an important determinant of substrate activity. The fact that AFC-val-ile-ser, AFC-val-ile, and AFC-val are substrates for the enzyme, although the latter two peptides are weaker substrates than the tetrapeptide, suggests that the nature of the amino acid residues attached to the modified cysteine residue is not of critical importance. The fact that an isoprenoid moiety is required for substrate activity suggests that inhibitors preferably include such a moiety. The observed steroselectivity and sterospecificity of the protease activity suggest that the L isomer is preferred for any amino acids or amino acid derivatives.

Preferred inhibitors are related to AFC-tripeptides wherein the bond between the cysteine and the peptide is resistant to proteolytic digestion. The design of protease resistant bonds is well known to those skilled in the art.

Using these guidelines we prepared the compounds listed in FIG. 5. The ability of these compounds to act as inhibitors was tested as described above. These molecules illustrate some of the possible inhibitors; the list is not intended to limit the invention.

Synthesis and Structure Confirmation

N-[$^3$H]-Acetyl-S-all-trans-farnesyl-L-Cys-D-Val-L-Ile The peptide was purified by HPLC (Rainin silica, 4.6×250 mm, hexane/isopropanol/TFA 92:8:0:0.01 as eluant at a flow rate of 1.5 mL/min with UV detection at 210 nm). The retention time of the L-D-L isomer was 8.60 min.

$^1$HNMR (DMSO-d$_6$, 500 MHz): 8.11 (1H,d,J=9.5 Hz), 8.09 (1H,d, J=7.5 Hz), 8.01 (1H,d,J=7.5 Hz), 5.15 (1H,t,J=8 Hz), 5.04 (2H,t,J=8 Hz), 5.04 (2H,t,J=8 Hz), 4.59 (1H,dd, J=8,15 Hz), 4.34 (1H,dd, J=6,9 Hz), 4.18 (1H,dd, J=6.5,8.5 Hz), 3.17 (2H,dd, J=4,7.5 Hz), 2.65 (1H,dd,J=6.5,13.5 Hz), 2.51 (1H,dd,J=7.5,13.5 Hz), 2.08–1.90 (9H,m), 1.80 (3H,s), 1.79 (1H,m), 1.61 (3H,s), 1.60 (3H,s), 1.54 (6H,s), 1.38 (1H,m), 1.19 (1H,m), 0.79–25 0.87 (12H,m).

N-[$^3$H]-Acetyl-S-all-trans-farnesyl-L-Cys-L-Val-D-ile The retention time of the L-L-D isomer was 8.19 min.

$^1$HNMR (DMSO-d$_6$, 500 MHz) 8.19 (1H,d,J=8.5 Hz), 7.89 (1H,brs), 7.77 (1H,d,J=8.5 Hz), 5.14 (1H,t,J=8 Hz), 5.04 (2H,t,J=6 Hz), 4.46 (1H,dd,J=7,9 Hz), 4.26 (1H,dd,J= 6,13 Hz), 4.15 (1H,brs), 3.15 (1H,d,J=8 Hz), 3.12 (1H,d,J=8 Hz), 2.73 (1H,dd,J=5.5, 12.5 Hz), 2.51 (1H, dd, J=8.5,12.5 Hz), 2.06–1.90 (9H,m), 1.83 (3H,s), 1.78 (1H,m), 1.61 (3H,s), 1.60 (3H,s), 1.53 (6H,s), 1.39 (1H,m), 1.18 (1H,m), 0.79–0.84 (12H,m).

N-r$^3$HI-Acetyl-S-all-trans-farnesyl-L-Cys-L-Val-L-ile-D-Met or N-[$^3$H]acetyl-S-all-trans-farnesyl-L-(SEQ ID NO: 2)

The peptide was purified by HPLC chromatography (Rainin silica, 250×4.6 mm, 1.5 ml/min, hexane/isopropanol/TFA 90:10:0.01, uv detection was at 210 nm). The retention time was 9.38 min.

$^1$HNMR: (DMSO-d$_6$, 500 MHz) 8.15 (1H,d,J=8 Hz), 8.13 (1H,d,J=8.5 Hz), 7.86 (1H,d,J=9 Hz), 7.75 (1H,d,J=8.5 Hz), 5.15 (1H,t,J=7 Hz), 5.04 (2H,d,J=3.5 Hz), 4.46 (1H,dd,J=8, 14 Hz), 4.28–4.16 (3H,m), 3.13 (2H,d,J=7.5 Hz), 2.71 (1H,dd,J=6,14 Hz), 2.51 (1H,dd,J=8.5,14 Hz), 2.46–2.39 (3H,m), 1.99 (3H,s), 2.03–1.90 (10H,m), 1.82 (3H,s), 1.68 (1H,m), 1.61 (3H,s), 1.59 (3H,s), 1.53 (6H,s), 1.39 (1H,m), 1.03 (1H,m), 0.78 (12H,m).

N-[$^3$H]-Acetyl-S-all-trans-farnesyl-L-Cys-L-Val-L-ile-L-Met or N-[$^3$H]acetyl-S-all-trans-farnesyl-L-(SEQ ID NO: 2)

The peptide was purified by HPLC (Rainin silica, 250×4.6 mm, 1.5 ml/min, hexane/isopropanol/TFA 90:10:0.01, uv detection was at 210 nm). The retention time was 6.68 min.

$^1$HNMR:(DMSO-d$_6$, 500 MHz) 8.14 (1H,d,J=8 Hz), 8.12 (1H,d,J=8 Hz), 7.85 (1H,d,J=8.5 Hz), 7.81 (1H,d,J=9.5 Hz), 5.15 (1H,t,J=8 Hz), 5.05 (2H,m), 4.46 (1H,ddd,J=2,6,14.5 Hz), 4.39 (1H,dd,J=5,5,9.5 Hz), 4.33 (1H,ddd,J=5,10,14 Hz), 4.23 (1H,dd,J=7,8.5 Hz), 3.17 (1H,dd,J=8,14 Hz), 3.12 (1H,dd,J=7.5,14 Hz), 2.74 (1H,dd,J=6,13.5 Hz), 2.52 (1H, dd,J=7.5,13.5 Hz), 2.46–2.35 (3H,m), 2.00 (3H,s), 2.04–1.90 (10H,m), 1.83 (3H,s), 1.61 (3H,s), 1.60 (3H,s), 1.53 (6H,s), 1.24 (2H,m), 30 1.08 (1H,m), 0.80 (12H,m).

N-[$^3$H]-Acetyl-S-trans-geranyl-L-Cys-L-Val-L-ile

The peptide was purified by HPLC (Rainin silica, 250×4.6 mm, 1.5 ml/min, hexane/isopropanol/TFA 92:8:0.01; uv detection was at 210 nm). The retention time of the L-L-L isomer was 9.65 min.

$^1$HNMR (DMSO-d$_6$, 500 MHz):8.11 (1H,d,J=8HZ), 7.89 (1H,d,J=8 Hz), 7.76 (1H,d,J=8.5 Hz), 5.15 (1H,t,J=8 Hz), 5.03 (1H,t,J=6.5 Hz), 4.46 (1H,dd,J=8.5,9 Hz), 4.25 (1H, dd,J=7,9 Hz), 4.12 (1H,dd,J=6.8 Hz), 3.13 (2H,t,J=9 Hz), 2.72 (1H,dd,J=6,14 Hz), 2.53 (1H,dd,J=9,14 Hz), 1.94–2.08 (5H,m), 1.96 (1H,m), 1.83 (3H,s), 1.61 (3H,s), 1.59 (3H,s), 1.54 (3H,s), 1.40 (1H,m), 1.18 (1H,m), 0.78–0.88 (12H,m).

N-[$^3$H]-Acetyl-S-all-trans-geranylgeranyl-L-Cys-L-Val-L-ile

The peptide was purified by HPLC (Rainin silica, 250×4.6 mm, 1.5 ml/min, hexane/isopropanol/TFA 92:8:0.01; uv detection was at 210 nm). The retention time of the L-L-L isomer was 7.08 min.

$^1$HNMR (DMSO-d$_6$, 500 MHz):8.11 (1H,d,J=8 Hz), 7.89 (1H,d,J=8 Hz), 7.76 (1H,d,J=8.5 Hz), 5.15 (1H,t,J=8 Hz), 5.03 (1H,t,J=6.5 Hz), 4.46 (1H,dd, J=8.5,9 Hz), 4.25 (1H, t,J=7 Hz), 4.11 (1H,t,J=6 Hz), 3.12 (2H,d,J=6.5 Hz), 2.73 (1H,dd,J=5.5,13.5 Hz), 2.53 (1H,dd,J=8.5,13.5 Hz), 1.92–2.08 (13H,m), 1.83 (3H,s, 1.76 (1H,m), 1.61 (3H,s), 1.60 (3H,s), 1.54 (9H,s), 1.41 (1H,m), 1.17 (1H,m), 0.78–0.86 (12H,m).

N-[$^3$H]-acetyl-S-all-trans-farnesyl-L-Cys-L-Val-L-Ile-L-Met

A solution of N-[$^3$H]-acetyl-S-all-trans-farnesyl-L-Cys-L-Val-L-Ile-L-Met methyl ester (Ma et al., 1992 supra) (0.588 mCi, 2.35 μmol, 250 mCi/mmol) in aqueous 10%

Na$_2$CO$_3$ (10 mL) in CH$_3$OH: CH$_3$CN (1:1, 10 mL) was stirred at room temperature for 16 h. The reaction mixture was acidified to pH=2 with aqueous 10% HCl. The combined organic layers were washed with brine, dried over anhydrous MgSO$_4$, filtered, and evaporated. The residue was purified by normal phase HPLC (Rainin silica, 250–4.6 mm, 1.5 mL/min, hexane/isopropanol/TFA (90:10:0.01), UV detection was at 210 nm). The retention time was 6.68 min. Recovery of radioactivity: 0.29 mCi, 49%.

$^1$H NMR (DMSO-d$_6$, 500 MHz) of the authentic non-radioactive peptide: 8.14 (1H,d,J=8 Hz), 8.12 (1H,d,J=8 Hz), 7.85 (1H,d,J=8.5 Hz), 7.81 (1H,d,J=9.5 Hz), 5.15 (1H,t,J=8 Hz), 5.05 (2H,m), 4.46 (1H,ddd,J=2,6,14.5 Hz), 4.39 (1H,dd,J=5.5,9.5 Hz), 4.33 (1H,ddd,J=5,10,4 Hz), 4.23 (1H,dd,J=7,8.5 Hz), 3.17 (1H,dd,J=8,14 Hz), 3.12 (1H,dd, J=7.5,14 Hz), 2.74 (1H,dd,J=6,13.5 Hz), 2.52 (1H,dd,J=7.5, 13.5 Hz), 2.46–2.35 (3H,m), 2.00 (3H,s), 2.04–1.90 (10H, m), 1.83 (3H,s), 1.61 (3H,s), 1.60 (3H,s), 1.53 (6H,s), 1.24 (2H,m), 1.08 (1H,m), 0.80 (12H,m).

N-Boc-S-all-trans-farnesyl-L-cysteine

To a solution of cysteine (1.07 g, 8.83 mmol) in saturated NH$_3$-MeOH (40 mL) at 0° C. was added all-trans-farnesyl bromide (2.39 mL, 2.52 g, 8.83 mmol) in one portion (Brown et al., 1991). The mixture was stirred at 0° C. for 1 h, then at room temperature overnight. The solvent was evaporated and the residue dried under vacuum. The residue was dissolved in DCM (45 mL), followed by the addition of di-tert-butyl dicarbonate (2.89 g, 13.2 mmol) and triethylamine (1.85 mL, 1.34 g, 13.2 mmol). The mixture was stirred at room temperature for 18 h. The solvent was evaporated and the residue extracted with EtOAc (3×100 mL). The combined organic layer was washed with aqueous 5% HCl, then with brine, then dried over anhydrous MgSO$_4$, filtered, and evaporated. The residue was purified by silica gel chromatography (hexane/acetone 80:20,70:30) to give the title compound (2.95 g, 79%).

$^1$H NMR (CDCl$_3$, 500 MHz): 5.34 (1H,brs), 5.22 (1H,t, J=8 Hz), 5.09 (2H,t,J=6 Hz), 4.49 (1H,brs), 3.20 (2H,m), 2.96 (1H,dd,J=4, 13.5 Hz), 2.88 (1H,dd,J=5,13.5 Hz), 2.12–2.02 (6H,m), 1.96 (2H,t,J-9 Hz), 1.67 (3H,s), 1.66 (3H,s), 1.59 (6H,s), 1.45 (9H,s).

N-Boc-S-all-trans-farnesyl-L-cysteine Methyl Ester

To a solution of cysteine methyl ester hydrochloride (1.16 g, 6.78 mmol) in saturated NH$_3$-MeOH (40 mL) at 0C was added all-trans-farnesyl bromide (1.84 mL, 1.93 g, 6.78 mmol) in one portion (Brown et al., 1991). The mixture was stirred at 0° C. for 1 h, then at room temperature overnight. The solvent was evaporated and the residue dried under vacuum. The residue was dissolved in DCM (40 mL) followed by the addition of ditert-butyl dicarbonate (2.22 g, 10.1 mmol) and triethylamine (1.42 mL, 1.03 g, 10.1 mmol). The mixture was stirred at room temperature for 16 hours. The solvent was evaporated and the residue extracted with EtOAc (3×100 mL). The combined organic layers were washed with aqueous 5% HCl, saturated NaHCO$_3$, brine, dried over anhydrous MgSO$_4$, filtered, and evaporated. The residue was purified by silica gel chromatography (hexane/ acetone 80:20) to give the title compound (2.77 g, 93%).

$^1$H NMR (CDCl$_3$, 500 MHz): 5.30 (1H,d,J=7.5 Hz), 5.21 (1H,t,J=7.5 Hz), 5.09 (2H,brs), 4.52 (1H,brs), 3.76 (3H,s), 3.16 (2H,m), 2.91 (1H,dd,J=3.5, 13.5 Hz), 2.85 (1H,dd,J= 6,13.5 Hz), 2.12–1.95 (8H,m), 1.68 (3H,s), 1.66 (3H,s), 1.60 (6H,s), 1.44 (9H,s).

N-Boc-S-all-trans-farnesyl-L-cysteine Aldehyde (2)

To a solution of N-Boc-S-all-trans-farnesyl-L-cystein methyl ester (1.40 g, 3.19 mmol) in dry toluene (10 mL) at −60° C. was added diisobutylaluminum hybride (McNulty & Still, 1992) (1.0M in toluene, 8.00 mL, 8.00 mmol) over a 90 min period. After 2 h at −60° C., dry methanol (2.0 mL) was carefully added, followed by aqueous 10% potassium sodium tartrate tetrahydrate (20 mL, 7.00 g, 24.8 mmol). The mixture was stirred at room temperature for 2 h until two layers formed. The toluene layer was separated and the aqueous layer extracted with EtOAc (3×100 mL). The combined organic layers were washed with aqueous 5% HCl, and with brine, dried over anhydrous MgSO$_4$, filtered, and evaporated. Due to the compound's relative instability, the crude material was used directly in the next step without further purification.

$^1$H NMR (CDCL$_3$, 500 MHz): 9.67 (1H,d,J=8 Hz), 5.34 (1H,brs), 5.22 (1H,t,J=8 Hz), 5.09 (2H,t,J=6 Hz), 4.49 (1H,brs), 3.20 (2H,m), 2.96 (1H,dd,J=4,13.5 Hz), 2.88 (1H, dd,J=5,13.5 Hz), 2.12–2.02 (6H,m), 1.98–1.90 (2H,m), 1.67 (3H,s), 1.66 (3H,s), 1.59 (6H,s), 1.45 (9H,s).

N-Boc-S-all-trans-farnesyl-L-Cys-$^\Psi$(CH$_2$—NH) -L-Val (7)

To a mixture of N-Boc-S-all-trans-farnesyl-L-cysteinal (668 mg, 1.63 mmol) and L-valine (230 mg, 1.97 mmol) in 1% AcOH-MeOH (7.0 mL) was added dropwise a solution of sodium cyanobrohydride (Rodriguez, 1986) (240 mg, 3.87 mmol) in MeOH (3.0 mL) over a 30 min period. The reaction mixture was stirred for an additional 2 h, then concentrated under reduced pressure. The residue was dissolved in saturated aqueous NaHCO$_3$ (20 mL) and extracted with EtOAc (3×50 mL). The combined organic layers were washed with aqueous 5% HCl, and with brine, dried over anhydrous MgSO$_4$, filtered, and evaporated. The residue was purified by normal phase HPLC (Rainin silica, 250× 4.6mm, 2.5 mL/min, hexane/isopropanol/TFA (95:5:0.01), UV detection was at 210 nm). The retention time was 4.80 min.

$^1$H NMR (DMSO-d6, 500 MHz): 8.80 (1H,brs), 8.53 (1H,brs), 6.71 (1H,d,J=8.9 Hz), 5.14 (1H,t,J=7.9 Hz), 5.04 (2H,t,J=5.9 Hz), 3.55 (1H,brs), 3.28 (2H,d,J-11.5 Hz), 3.09 (1H,d,J=7.9), 2.83 (1H,d,J=5.5 Hz), 2.62–2.52 (2H,m), 2.42–2.32 (2H,m), 2.06–1.92 (6H,m), 1.94–1.86 (2H,m), 1.61 (3H,s), 1.59 (3H,s), 1.53 (6H,s), 1.35 (9H,s), 0.83 (6H,t,J-7 Hz).

N-Boc-S-all-trans-farnesyl-L-Cys-$^\Psi$(CH$_2$—NH)-L-Val-L-Ile(8)

To a mixture of N-Boc-S-all-trans-farnesyl-L-cysteinal (602 mg, 1.47 mmol) and L-Val-L-Ile (406 mg, 1.76 mmol) in 1% AcOH-MeOH (6.0 mL) was added dropwise a solution of sodium cyanoborohydride (220 mg, 3.54 mmol) in MeOH (2.0 mL) over a 30 min period. The reaction mixture was stirred for an additional 2 h, then concentrated under reduced pressure. The residue was dissolved in saturated aqueous NaHCO$_3$ (30 mL) and extracted with EtOAc (3×50 mL). The combined organic layers were washed with aqueous 5% HCl, and with brine, dried over anhydrous MgSO$_4$, filtered, and evaporated. The residue was purified by normal phase HPLC (Rainin silica, 250 x 4.6mm, 2.5 mL/min, hexane/isopropanol/TFA (95:5:0.01), UV detection was at 210nm). The retention time was 3.50 min.

$^1$H NMR (DMSO-d$_6$, 500 MHz): 8.84 (1H,d,J=7.9 Hz), 8.57 (1H,brs), 6.94 (1H,d,J=8.9 Hz), 5.16 (1H,t,J-7.9 Hz), 5.05 (2H,t,J=5.9 Hz), 4.25 (1H,dd,J=8, 6 Hz), 3.88–3.76 (2H,m), 3.18 (1H,dd,J=13, 8 Hz), 3.11 (1H, dd, J=13, 8 Hz), 2.97 (1H,brs), 2.89 (1H,brs), 2.52 (2H,d,J=7 Hz), 2.28–2.16 (1H,m), 2.06–1.92 (6H,m), 1.94–1.88 (2H,m), 1.86–1.80 (1H,m), 1.61 (3H,s), 1.59 (3H,s), 1.53 (6H,s), 1.38 (9H,s), 1.22–1.19 (1H,m), 1.15 (3H,t,J=7 Hz), 1.01 (3H,d,J=7 Hz), 0.92 (3H, d, J=7 Hz), 0.88–0.83 (5H,m).

N-Boc-S-all-trans-farnesyl-L-Cys-$^\Psi$(CH$_2$—HN) -L-Val-L-Ile-L-Ser or N-Bos-S-all-trans-farnesyl-L-Cys-$^\Psi$(CH$_2$—HN)-(SEQ ID NO: 1) Methyl Ester To a mixture of N-Boc-S-all-trans-farnesyl-L-cysteinal (818 mg, 2.00 mmol) and L-Val-L-Ile-L-Ser methyl ester hydrochloride (820 mg, 2.19 mmol) in 1% AcOH-MeOH (7.0 mL) was added dropwise a solution of sodium cyanoborohydride (255 mg, 4.13 mmol) in MeOH (2.0 mL) over a 30 min period. The reaction mixture was stirred for an additional 2 h, then concentrated under reduced pressure. The residue was dissolved in saturated aqueous NaHCO$_3$ (30 mL) and extracted with EtOAc (3×50 mL). The combined organic layers were washed with 5% HCl, brine, dried over anhydrous MgSO$_4$, filtered, and evaporated. The residue was purified by normal phase HPLC (Rainin silica, 250×4.6mm, 2.5 mL/min, hexane/isopropanol/TFA (97:3:0.01), UV detection was at 210nm). The retention time was 8.91 min. $^1$H NMR (DMSO-d6, 500 MHz): 8.18 (1H,d,J=8 Hz), 8.10 (1H,d,J=8 Hz), 7.76 (1H,d,J=8.5 Hz), 7.79 (1H, d, J=9.5 Hz), 5.15 (1H,t,J=8 Hz), 5.05 (2H,m), 4.46 (1H, ddd, J=2, 6, 14.5 Hz), 4.39 (1H,dd,J=5.5, 9.5 Hz), 4.32 (1H,ddd,J=5, 10, 14 Hz), 4.23 (1H,dd,J=7, 8.5 Hz), 3.17 (1H,dd,J=8, 14 Hz), 3.12 (1H,dd,J=7.5, 14 Hz), 2.74 (1H,dd,J=6, 13.5 Hz), 2.52 (1H,dd,J=7.5, 13.5 Hz), 2.46–2.35 (3H,m), 2.00 (3H,s), 2.04–1.90 (10H,m), 1.63 (3H,s), 1.61 (3H,s) 1.60 (3H,s), 1.53 (6H,s), 1.24 (2H,m), 1.08 (1H,m), 0.80 (12H,m).

N-Boc-S-all-trans-farnesyl-L-Cys-$^\psi$(CH$_2$—NH)-L-Val-L-Ile-L-Ser or N-Bos-S-all-trans-farnesyl-L-Cys-$^\psi$(CH$_2$—HN)-(SEQ ID NO: 1)

A mixture of N-Boc-S-all-trans-farnesyl-L-Cys-$^\psi$(CH$_2$—NH)-L-Val-L-Ile-L-Ser methyl ester (110 mg, 0.13 mmol) and 10% Na$_2$CO$_3$ (10 mL) in CH$_3$OH: CH$_3$CN (1:1, 10 mL) was stirred at room temperature for 16 h. The reaction mixture was acidified to pH=2 with aqueous 10% HCl. solution was extracted with EtOAc (3×40 mL) and the combined organic layers were washed with brine, dried over anhydrous MgSO$_4$, filtered and evaporated. The residue was purified by normal phase HPLC (Rainin silica, 250×4.6 mm, 2.5 mL/min, hexane/isopropanol/TFA (90:10:0.01), UV detection was at 210 nm). The retention time was 10.10 min.

$^1$H NMR (DMSO-d6, 500 MHz): 8.86 (1H,brs), 8.62 (1H,brs), 8.14 (1H,d,J=8 Hz), 8.12 (1H,d,J=8 Hz), 7.85 (1H,d,J=8.5 Hz), 7.81 (1H,d,J=9.5 Hz), 5.15 (1H, t, J=8 Hz), 5.05 (2H,m), 4.46 (1H,ddd,J=2, 6, 14.5 Hz), 4.39 (1H,dd, J=5.5, 9.5 Hz), 4.33 (1H,ddd,J=5, 10, 14 Hz), 4.23 (1H,dd, J=7, 8.5 Hz), 3.17 (1H,dd,J=8, 14 Hz), 3.12 (1H,dd,J=7.5, 14 Hz), 2.74 (1H,dd,J=6, 13.5 Hz), 2.52 (1H,dd,J=7.5, 13.5 Hz), 2.46–2.35 (3H,m), 2.00 (3H,s), 2.04–1.90 (10H,m), 1.83 (3H,s), 1.61 (3H, s), 1.60 (3H,s), 1.53 (6H,s), 1.24 (2H,m), 1.08 (1H, m), 0.80 (12H,m)).

N-Boc-S-all trans-farnesyl-L-cysteine-$\psi$(CH$_2$—NH)-L-ValL-Ile-L-Met or N-Boc-S-all-trans-farnesyl-L-Cys-$\psi$ (Ch$_2$—HN)-(SEQ ID NO: 2) Methyl Ester To a mixture of N-Boc-S-all-trans-farnesyl-L-cysteinal (690 mg, 1.69 mmol) and L-Val-L-Ile-L-Met methyl ester hydrochloride (830 mg, 2.01 mmol) in 1% AcOH-MeOH (6.0 mL) was added dropwise a solution of sodium cyanoborohydride (250 mg, 4.02 mmol) in MeOH (3.0 mL) over a 30 min period. The reaction mixture was stirred for an additional 2 h, then concentrated under reduced pressure. The residue was dissolved in saturated aqueous NaHCO$_3$ (20 mL) and extracted with EtOAc (3×50 ml). The combined organic layers were washed with aqueous 5% HCl, and with brine, dried over anhydrous MgSO$_4$, filtered, and evaporated. The residue was purified by normal phase HPLC (Rainin silica, 250×4.6 mm, 1.5 mL/min, hexane/isopropanol/TFA (97:3:0.01), UV detection was at 210 nm). The retention time was 11.80 min.

$^1$H NMR (DMSO-d6, 500 MHz): 8.14 (1H,d,J=8 Hz), 8.12 (1H,d,J=8 Hz), 7.85 (1H,d,J=8.5 Hz), 7.81 (1H, d, J=9.5 Hz), 5.15 (1H,t,J=8 Hz), 5.05 (2H,m), 4.46 (1H, ddd, J=2, 6, 14.5 Hz), 4.39 (1H,dd,J=5.5, 9.5 Hz), 4.33 (1H,ddd, J=5, 10, 14 Hz), 4.23 (1H,dd,J=7, 8.5 Hz), 3.17 (1H,dd,J=8, 14 Hz), 3.12 (1H,dd,J=7.5, 14 Hz), 2.74 (1H,dd,J=6, 13.5 Hz), 2.52 (1H,dd,J=7.5, 13.5 Hz), 2.46–2.35 (3H,m), 2.00 (3H,s), 2.04–1.90 (10H,m), 1.83 (3H,s), 1.61 (3H,s), 1.60 (3H,s), 1.53 (6H,s), 1.24 (2H,m), 1.08 (1H,m), 0.80 (12H, m).

N-Boc-S-all-trans-farnesyl-L-Cys-$\psi$(CH$_2$—NH)-L-Val-L-Ile-L-Met or N-Boc-S-all-trans-farnesyl-L-Cys-$\psi$(CH$_2$—HN)-(SEQ ID NO: 2).

A mixture of N-Boc-S-all-trans-farnesyl-L-Cys-$\psi$ (CH$_2$-NH)-L-Val-L-Ile-L-Met methyl ester (50 mg, 0.06 mmol) and aqueous barium hydroxide (Serafinowski., 1985) (0.25M, 200 µL, 4.4 mmol) in MeOH (5.0 mL) was stirred at room temperature for 32 h. The reaction mixture was acidified to pH=2 with aqueous 10% HCl. The solution was extracted with EtOAc (3×40 mL), the combined organic layers were washed with brine, dried over anhydrous MgSO$_4$, filtered, and evaporated. The residue was purified by normal phase HPLC (Rainin silica, 250×4.6 mm, 1.5 mL/min, hexane/isopropanol/TFA (97:3:0.01), UV detection was at 210 nm). The retention time was 21.20 min.

$^1$H NMR (DMSO-d6, 500 MHz): 9.94 (1H,brs), 8.57 (1H,brs), 8.37 (1H,d,J=7 Hz), 7.86 (1H,d,J=8 Hz), 6.68 (1H,d,J=9 Hz), 5.15 (1H,t,J=7.9 Hz), 5.05 (2H, t, J=5.9 Hz), 4.39–4.34 (1H. m), 4.22 (1H,t,J=8 Hz), 3.88–3.76 (2H,m), 3.18 (1H,dd,J=13, 8 Hz), 3.11 (1H, dd, J=13, 8 Hz), 2.87 (1H,brs), 2.89 (1H,brs), 2.52 (2H, d, J=7 Hz), 2.28–2.16 (1H,m), 2.06–1.92 (6H,m), 1.94–1.88 (2H,m), 1.86–1.80 (1H,m), 1.61 (3H,s), 1.59 (3H,s), 1.53 (6H,s), 1.44–1.40 (1H,m), 1.35 (9H,s), 1.12–1.04 (1H,m), 1.15 (3H,t,J=7 Hz), 0.84–0.77 (12, m).

N-Boc threo-4-hydroxy-5-(s-all-trans-farnesyl) thiomethyl-pyrrolidin-2-one

To a solution of N-Boc-S-all-trans-farnesyl cystein (1.54 g, 3.62 mmol) in DCM (40 mL) was added Meldrum's acid (Jouin et al., 1987) (cycloisopropylidene malonate, 575 mg, 3.99 mmol) and dimethylaminopyridine (DMAP, 1.02 g, 8.34 mmol). The mixture was cooled at −5° C., and a solution of isopropenyl chloroformate (IPCF, 435 µL, 480 mg, 3.92 mmol) in DCM (5.0 mL) was added dropwise with stirring. The mixture was stirred for 5 The reaction was quenched with cold 5% aqueous postssium bisulfate (25 mL), the organic layer separated, washed with bine, dried over anhydrous MgSO$_4$, filtered, and evaporated. The residue was dissolved in EtOAc (50 mL) and heated at reflux for 1 h. The solvent was evaporate and the residue dissolved in DCM:AcOH (10:1, 30 mL). The mixture was cooled to 0° C., and sodium borohydride (252 mg, 6.69 mmol) was added in one portion. The mixture was stirred at room temperature for 6 h. The reaction was quenched with water (10 mL), the organic layer separated, and washed with brine, dried over anhydrous MgSO$_4$, filtered, and evaporated. The residue was purified by silica gel chromatography (hexane/EtOAc 80:20, 70:30) to provide the title compound (642 mg).

$^1$H NMR (CDCl$_3$): 5.26 (1H,t,J=8 Hz), 5.09 (2H, brs), 4.62 (1H, brd, J=6.5 Hz), 4.31 (1H,ddd,J=2.5, 8.5, 15.5 Hz), 3.25 (2H,dd,J=4, 7 Hz), 3.07 (1H,dd,J=3, 13 Hz), 2.89 (1H,dd,J=10, 13 Hz), 2.77 (1H,dd,J=7.5, 17.5 Hz), 2.66 (1H,dd,J=7, 17.5 Hz), 2.57 (1H, brd, J=3 Hz), 2.12=1.94 (8H,m), 1.68 (6H,s), 1.59 (6H,s), 1.53 (9H,s).

(3S, 4S)-N-Boc-4-amino-3-hydroxy-5-(S-all-trans-farnesyl)-pentanoic acid

To a solution of N-Boc threo-4-hydroxy-5-(S-all-trans-farnesyl) thiomethyl-pyrrolidin-2-one (470 mg) in acetone (10 mL) was added 1N sodium hydroxide (2.0 mL) at 0° C.

The mixture was stirred at 0° C. for 1 h, then acidified to pH=6 with aqueous 10% HCl. The solvent was evaporated and the residue extracted with EtOAc (3×30 mL). The combined organic layers were washed with brine dried over anhydrous MgSO$_4$, filtered, and evaporated. The residue was purified by silica gel chromatography (hexane/acetone 80:20) to give the title compound (370 mg).

$^1$H NMR (CDCl$_3$ 500 MHz): 5.23 (1H,t,J=8 Hz), 5.09 (1H,t,J=7 Hz), 5.01 (1H,d,J=9.5 Hz), 4.35 (1H, d, J=10 Hz), 3.66 (1H,dd,J=7, 15 Hz), 3.19 (2H,d,J=8 Hz),2.71 (1H,dd, J=3, 16.5 Hz), 2.12–1.95 (8H,m), 1.67 (3H,s), 1.66 (3H, s), 1.59 (6H,s), 1.55 (9H,s).

(3S, 4S)-N-Boc-4-amino-3-hydroxy-5-(s-all-trans-farnesyl) -1-(L-isoleucine-L-methionine)pentanoic amide A solution of (3S, 4S)-N-BOc-4-amino-3-hydroxy-5-(S-all-trans-farnesyl)-1- (methyl L-isoleucine-L-methionine)-pentanoic amide (53 mg) and aqueous 10% sodium carbonate in CH$_3$OH:CH$_3$CN (1:1, 10 mL) was stirred at room temperature for 16 h. The reaction mixture was acidified to pH-2 with aqueous 10% HCl, extracted with EtOAc (3×40 mL). The combined organic layers were washed with brine, drived over anhydrous MgSO$_4$, filtered and evaporated. The residue was separated by silica gel chromatography (hexane/acetone 70:30, hexane/acetone/methanol 70:30:10) to give the title compound as a white solid (40 mg): $^1$HNMR (DMSO-d6): 7.50 (1H,brs), 6.34 (1H,brs), 5.16 (1H,t,J=8 Hz), 5.04 (2H,dd,J=6, 11.5 Hz), 4.10 (1H,dd,J=6.5, 8.5 Hz), 3.92 (1H,s), 2.49 (1H,dd,J=7, 15 Hz), 3.15 (2H,dd,J=4.5, 6.5 Hz), 2.60 (1H,dd,J=6, 14 Hz), 2.37 (3H,m), 1.96 (3H, s), 2.04–1.89 (10H,m), 1.81 (1H,m), 1.61 (3H,s), 1.60 (2H,s), 1.54 (6H,s), 1.41 (1H,m), 1.32 (9H,brs), 1.08 (1H,m), 0.80 (3H,d,J=6.5 Hz), 0.77 (3H,t,J=7.5 Hz).

(3S, 4S)-N-Boc-4-amino-3-hydroxy-5-(s-all-trans-farnesyl) -1-(methyl Ile-Met) pentanoic amide To a mixture of (3S, 4S)-N-Boc-4-amino-3-hydroxy-5- (S-all-trans-farnesyl)-pentanoic acid (185 mg, 0.394 mmol), L-Ile-L-Met methyl ester hydrochloride (231 mg, 0.592 mmol), 1-hydroxybenzotriazole monohydrate (80 mg, 0.59 mmol) and N-methylmorpholine (65 µL, 60 mg, 0.59 mmol) in DMF (10 mL) at 0° C. was added 1-ethyl-3-(3-dimethylamino-propyl)carbodiimide hydrochloride (98 mg, 0.51 mmol) in one portion. The mixture was stirred at 0° C. for 2 h, then at room temperature for 46 h. The reaction was quenched with water (20 mL) and extracted with EtOAc (3×40 mL). The combined organic layer were washed with aqueous 10% HCl, saturated NaHCO$_3$, brine, dried over anhydrous MgSO$_4$, filtered, and evaporated. The residue was purified by silica gel chromatography (hexane/acetone 70:30, 60:40) to give the title compound (188 mg, 66%).

$^1$H NMR (CDCl$_3$, 500 MHz): 6.93 (1H,d,J=8 Hz), 6.66 (1H,d,J=8.5 Hz), 5.22 (1H,t,J=8 Hz), 5.08 (2H, t, J=4.5 Hz), 5.04 (1H,d,J=9.5 Hz), 4.70 (1H,dd,J=7.5, 12.5 Hz), 4.32 (1H,t,J=6.5 Hz), 4.27 (1H, brd, J=9 Hz), 4.18 (1H,s), 3.74 (2H,s), 3.64 (1H,dd,J=8, 15.5 Hz), 3.17 (2H,dd,J=4.5, 6.5 Hz), 2.71 (1H,dd,J=8, 13.5 Hz), 2.64 (1H,dd,J=6, 13.5 Hz), 2.50 (2H,t,J=7 Hz), 2.47 (1H), 2.34 (1H,dd,J=3, 16 Hz), 2.08 (2H,s), 2.17–1.94 (10H,m), 1.87 (2H,m), 1.66 (3H,s), 1.65 (3H,s), 1.58 (6H,s), 1.52 (1H,m), 1.44 (9H,s), 1.15 (1H,m), 0.92 (3H,d,J=6.5 Hz), 0.90 (3H,t,J=8 Hz).

(3S, 4S)-N-Boc-4-amino-3-hydroxy-5-(S-all-trans-farnesyl) -1-(methyl L-Val-L-Ile-L-Met) pentanoic Amide To a mixture of (3S, 4S)-N-Boc-4-amino-3-hydroxy-5- (S-all-trans-farnesyl)-pentanoic acid (185 mg, 0.394 mmol), L-Val-L-Ile-L-Met methyl ester hydrochloride (289 mg, 0.592 mmol), 1-hydroxybenzotriazole monohydrate (80 mg, 0.59 mmol) and N-methylmorpholine (65 µl, 60 mg, 0.59 mmol) in DMF (10 mL) at 0° C. was added 1-ethyl-3-(3-dimethylaminopropyl) carbodiimide hydrochloride (98 mg, 0.51 mmol) in one portion. The mixture was stirred at 0° C. for 2 h, then at room temperature for 25 h. The reaction was quenched with water (20 mL) and extracted with EtOAc (3×40 mL). The combined organic layer were washed with aqueous 10% HCl, saturated NaHCO$_3$, brine, dried over anhydrous MgSO$_4$, filtered, and evaporated. The residue was purified by silica gel chromatography (hexane/acetone 70:30, 60:40, 50:50) to give the title compound (228 mg, 70%).

$^1$H NMR (CDCl$_3$ 500 MHz): 7.42 (1H,brs), 7.20 (1H, brs), 7.16 (1H,brs), 5.23 (1H,t,J=7 Hz), 5.10 (2H, t, J=5 Hz), 4.74 (1H,ddd,J=4.5, 7.5, 12.5 Hz), 4.43 (2H, m), 4.26 (1H,d,J=10 Hz), 3.75 (3H,s), 3.60 (,1H, dd, 8, 15 Hz), 3.17 (2H,t,J=7.5 Hz), 2.72 (1H,dd,J=8, 14 Hz), 2.64 (1H, dd, 6, 14 Hz), 2.53 (1H,dd,J-9.5, 14.5 Hz), 2.47 (2H,t,J=7 Hz), 2.42 (1H), 2.05 (3H,s), 2.16–1.96 (13H,m), 1.82 (1H,m), 1.67 (3H,s), 1.65 (3H,s), 1.59 (3H,s), 1.58 (3H,s), 1.53 (1H,m), 1.43 (9H,s), 1.10 (1H,m), 0.90 (12H,m).

(3S 4S)-N-Boc-4-amino-3-hydroxy-5-(S-all-trans-farnesyl) -1-(L-Val-L-Ile-L-Met) pentanoic Amide A mixture of (3S, 4S)-N-Boc-4-amino-3-hydroxy-5-(S-all-trans-farnesyl)-1-(methyl L-Val-L-Ile-L-Met) pentanoic amide (228 mg) and 10% Na$_2$CO$_3$ (20 mL) in CH$_3$OH:CH$_3$CN (1:1, 10 mL) was stirred at room temperature for 40 h. The reaction mixture was acidified to pH=2 with aqueous 10% HCl. The solution was extracted with EtOAc (3×40 mL) and the combined organic layers were washed with brine, dried over anhydrous MgSO$_4$, filtered, and evaporated. The residue was separated by silica gel chromatography (hexane/acetone 70:30, hexane/acetone/methanol 70:30:10) to give the title compound (174 mg) as a white solid.

$^1$H NMR (DMSO-d6, 500 MHz): 7.92 (1H,d,J=8 Hz), 7.82 (1H,d,J=7 Hz), 7.40 (1H,brs), 6.40 (1H,d,J=9 Hz), 5.15 (1H,t,J=8 Hz), 5.04 (1H,dd,J=6.5, 12.5 Hz), 4.91 (1H,brs), 4.22 (1H,t,J=8 Hz), 4.10 (1H,t,J=8 Hz), 3.94 (1H,brs), 3.88 (1H,s), 3.51 (1H,dd,J=9, 16 Hz), 3.10 (2H,d,J=6.5 Hz), 2.59 (1H,dd,J=5, 13 Hz), 2.32 (3H,m), 1.95 (3H,s), 2.12=1.88 (10H,m), 1.74 (3H,m), 1.61 (3H, s) , 1.59 (3H,s) , 1.53 (6H,s) , 1. 40 (1H,m) , 1.36 (9H, s), 1.04 (1H,m), 0.79 (12H,m).

(4S)-N-Boc-4-amino-2-difluoro-3-hydroxy-5-(S-all-trans-farnesyl)-pentanoate Ethyl Ester To a suspension of zinc dust (764 mg, 11.7 mmol) in anhydrous THF (30 mL) was added one crystal of I$_2$ (Doherty et al., 1992). The reaction mixture heated to ref lux and ethyl bromodifluoroacetate (100 µL) was added to initiate the reaction. After 2 min, a mixture of the N-BOc-S-all-trans-farnesyl-L-cysteinal (2.42 g, 5.86 mmol), ethyl bromodifluoroacetate (1.12 mL, 1.79 g, 8.83 mmol) in THF (15 mL) was added at such a rate as to control the ref lux (as rapidly as possible). After heating at ref lux for 30 minutes, the mixture was allowed to cool, then partitioned between EtOAc (100 mL) and aqueous 1M KHSO$_4$ (100 mL). The organic layer was separated, and the aqueous phase extracted with EtOAc (2×100 mL). The combined organic layers were washed with brine, dried over anhydrous MgSO$_4$. After concentration, the residue was purified by repeated silica gel chromatography (hexane/EtOAc 90:10, 85:15) to provide (N-Boc-S-all-trans-farnesyl)-L-cysteine methyl ester (844 mg), N-Boc-S-all-trans-farnesyl-L-cysteinol (1, 141 mg), and (4S) -N-Boc-4-amino-2, 2-difluoro-3-hydroxy-5- (S-all-trans-farnesyl)pentanoic ethyl ester (531 mg).

N-Boc-S-all-trans-farnesyl-L-cysteinol

¹H NMR (CDCl₃ 500 MHz): 5.24 (1H,t,J=8 Hz), 5.09 (2H,t,J=7 Hz), 4.99 (1H,brs), 3.74 (3H,m), 3.18 (2H, dd, J=2, 8 Hz), 2.68 (1H,dd,J=6, 13 Hz), 2.63 (1H, dd, J=7, 13 Hz), 2.07 (6H,m), 1.97 (2H,t,J=8 Hz), 1.68 (3H, s), 1.67 (3H,s), 1.60 (6H,s), 1.45 (9H,s).

(4S)-N-Boc-4-amino-2-difluoro-3-hydroxy-5-(S-all-trans-farnesyl)pentanoate ethyl ester ¹H NMR (CDCl₃ 500 MHz): 5.24 (1H,t,J=7 Hz), 5.09 (2H,t,J=5.5 Hz), 5.04 (1H,brs), 4.35 (3H,m), 3.95 (1H,dd, J=7, 14 Hz), 3.87 (1H,brs), 3.20 (2H,dd,J-3, 8 Hz), 2.77 (2H,brs), 2.06 (6H,m), 1.96 (2H,t,J=8 Hz), 1.67 (6H,s), 1.59 (6H,s), 1.43 (9H,s), 1.36 (3H,t,J-7 Hz).

(4S)-N-Boc-4-amino-2.2-difluoro-3-hydroxy-5-(S-all-trans-farnesyl)-pentanoic acid A mixture of (4S)-N-Boc-4-amino-2-difluoro-3-hydroxy-5-(S-all-trans-farnesyl)pentanoate ethyl ester (141 mg) and aqueous 5% KOH in methanol (5.0 mL) was stirred at 0° C. for 2 h. The reaction was acidified to pH=2 with aqueous 10% HCl, and extracted with EtOAc (3×50 mL). The combined organic layers were washed with aqueous 10% HCl, brine, dried over anhydrous MgSO₄, filtered, and evaporated. The residue was purified by silica gel chromatography (hexane/EtOAc 80:20) to provide the title compound (131 mg).

¹H NMR (DMSO-d6, 500 MHz): 5.17 (1H,t,J=7 Hz), 5.05 (2H,t,J=5 Hz), 4.18 (1H,dd,J=7, 14 Hz), 3.87 (1H, t, J=5 Hz), 3.14 (2H,d,J=6 Hz), 2.55 (1H,dd,J=6, 13 Hz), 2.46 (1H,dd,J=8, 13 Hz), 2.04 (6H,m), 1.92 (2H, t, J=7 Hz), 1.68 (3H,s), 1.67 (3H,s), 1.57 (6H,s), 1.38 (9H,s).

(4S)-N-Boc-4-amino-2 2-difluoro-3-hydroxy-5-(S-all-trans-farnesyl)-1-(methyl L-Ile-L-Met)pentanoic Amide A mixture of (4S)-N-Boc-4-amino-2,2-difluoro-3-hydroxy-5-(s-all-trans-farnesyl)pentanoic acid (233 mg, 0.46 mmol), 1-Ile-L-Met methyl ester hydrochloride (270 mg, 0.69 mmol), 1-hydroxybenzotriazole monohydrate (93 mg, 0.69 mmol) and N-methylmorpholine (76 µL, 70 mg, 0.69 mmol) in DMF (10 mL) at 0° C. was added 1-ethyl-3-(3-dimethylamino-propyl)carbodiimide hydrochloride (106 mg, 0.55 mmol) in one portion. The mixture was stirred at 0° C. for 2 h, then at room temperature for 13 h. The reaction was quenched with water (20 mL) and mixture extraced with EtOAc (3×50 mL). The combined organic layers were washed with aqueous 10% HCl, saturated NaHCO₃, brine, dried over anhydrous MgSO₄, filtered, and evaporated. The residue was purified by silica gel chromatography (hexane/EtOAc 85:15) to give the title compound (155 mg, 44%).

¹H NMR (CDCl₃ 500 MHz): 7.23 (1H,d,J=5.5 Hz), 7.18 (1H,d,J=8 Hz), 5.28 (1H,d,J=8.5 Hz), 5.22 (1H, t, J=8 Hz), 5.08 (2H,t,J=7 Hz), 4.71 (1H,dd,J=5, 13 Hz), 4.41 (1H,m), 4.34 (1H,t,J=6 Hz), 4.07 (1H,brs), 3.99 (1H,dd,J=7, 14 Hz), 3.73 (3H,s), 3.18 (2H,dd,J=3, 8 Hz), 2.80 (1H,dd,J=5.5, 12.5 Hz), 2.72 (1H,dd,J=7.5, 12.5 Hz), 2.51 (2H,t,J=7 Hz), 2.07 (3H,s), 2.19–1.93 (10H,m), 1.81 (1H,brs), 1.67 (3H,s), 1.65 (3H,s), 1.59 (6H,s), 1.53 (1H,m), 1.43 (9H,s), 1.18 (1H,m), 0.94 (6H,m).

(4S)-N-Boc-4-amino-2 2-difluoro-3-hydroxy-5-(S-all-trans-farnesyl)-1-(methyl L-Val-L-Ile-L-Met)pentanoic Amide A mixture of (4S)-N-Boc-4-amino-2,2-difluoro-3-hydroxy-5-(S-all-trans-farnesyl)pentanoic acid (277 mg, 0.55 mmol), L-Val-L-Ile-L-Met methyl ester hydrochloride (402 mg, 0.82 mmol), 1-hydroxybenzotriazole monohydrate (111 mg, 0.82 mmol) and N-methylmorpholine (90 µl, 83 mg, 0.82 mmol) in DMF (8.0 mL) at 0° C. was added 1-ethyl-3-(3-dimethylaminopropyl)-carbodiimide hydrochloride (126 mg, 0.66 mmol) in one portion. The mixture was stirred at 0° C. for 2 h, then at room temperature for 21 h. The reaction was quenched with water (20 mL) and extracted with EtOAc (3×50 mL). The combined organic layers were washed with aqueous 10% HCl, saturated NaHCO₃, brine, dried over anhydrous MgSO₄, filtered, and evaporated. The residue was purified by silica gel chromatography (hexane/acetone 90:10, 85:15) to give the title compound (90 mg, 19%).

¹H NMR (CDCl₃ 500 MHz): 7.28 (1H,d,J-7 Hz), 7.18 (1H,d,J=9 Hz), 6.85 (1H,s), 5.32 (1H,d,J=7.5 Hz), 5.23 (1H,t,J=6.5 Hz), 5.08 (2H,s), 4.69 (1H,ddd,J=5, 8, 12.5 Hz), 4.35 (3H,m), 3.98 (1H, brd, J=5 Hz), 3.74 (3H,s), 3.19 (2H,d,J=7 Hz), 2.80 (1H,dd,J=6, 13 Hz), 2.73 (1H,dd,J=7, 13 Hz), 2.49 (2H,t,J=8hz), 2.07 (3H, s), 2.25–194 (11H,m), 1.89 (1H,m), 1.67 (6H,s), 1.60 (6H,s), 1.51 (1H,m), 1.43 (9H,s), 1.15 (1H,m), 0.92 (12H,m).

(4S)-N-Boc-4-amino-2,2-difluoro-3-hydroxy-5-(S-all-trans-farnesyl)-1-(L-Ile-L-Met)pentanoic Amide A mixture of (4S)-N-Boc-4-amino-2,2-difluoro-3-hydroxy-5-(S-all-trans-farnesyl)-1-(methyl L-Ile-L-Met) pentanoic amide (155 mg, 0.21 mmol) and aqueous 10% sodium carbonate (10 mL) in CH₃CN:CH₃OH (1:1, 10 mL) was stirred at room temperature for 36 h. The mixture was acidified to pH=2 with aqueous 10% HCl. The mixture was extracted with EtOAc (3×50 mL) and the combined organic layers were washed with aqueous 10% HCl, brine, dried over anhydrous Na₂SO₄, filtered, and evaporated. The residue was purified by silica gel chromatography (hexane/acetone 70:30, 50:50, acetone, methanol) to give the title compound (90 mg, 59%) as a solid.

¹HNMR (DMSO-d6, 500 MHz): 6.26 (1H,d,J=9 Hz), 5.15 (1H,t,J=8 Hz), 5.04 (2H, brd, J=6 Hz), 4.13 (3H,m), 3.92 (1H,dd,J=8, 16 Hz), 3.14 (2H,m), 2.54 (1H, dd, J=8, 13.5 Hz), 2.44 (1H,dd,J=7, 13.5 Hz), 2.41 (2H, t, J=8 Hz), 1.98 (3H,s), 2.05–1.78 (11H,m), 1.61 (6H,s), 1.53 (6H,s), 1.46 (1H,m), 1.34 (9H,s), 1.06 (1H,m), 0.84 (3H,d,J=7 Hz), 0.79 (3H,t,J=7 Hz).

(4S)-N-Boc-4-amino-2,2-difluoro-3-hydroxy-5-(S-all-trans-farnesyl)-1-(L-Val-L-Ile-L-Met)pentanoic Amide A mixture of (4S)-N-Boc-4-amino-2,2-difluoro-3-hydroxy-5-(S-all-trans-farnesyl)-1-(methyl L-Val-L-Ile-L-Met)pentanoic amide (90 mg) and aqueous 10% sodium carbonate (10 mL) in CH₃CN:CH₃OH (1:1, 10 mL) was stirred at room temperature for 60 h. The mixture was acidified to pH=2 with aqueous 10% HCl. The mixture was extracted with EtOAc (3×50 mL) and the combined organic layers were washed with aqueous 10% HCl, brine, dried over anhydrous Na₂SO₄, filtered, and evaporated. The residue was purified by silica gel chromatography (hexane/acetone 70:30, 50:50, acetone, methanol) to give the title compound (35 mg, 40%) as a solid.

¹H NMR (DMSO-d6, 500 MHz): 7.25 (2H,brs), 6.65 (2H,brs), 5.15 (1H,t,J=7 Hz), 5.04 (2H,t,J=5 Hz), 4.22 (1H,d,J=8 Hz), 4.16 (1H,dd,J=8, 21.5 Hz), 4.12 (1H, d, J=6.5 Hz), 3.91 (1H,t,J=9 Hz), 3,89 (1H,brs), 3.13 (2H, m), 2.54 (1H,dd,J=9, 13.5 Hz), 2.43 (1H,dd,J=7, 13.5 Hz), 2.35 (3H,m), 1.95 (3H,s), 2.07–1.88 (10H,m), 1.76 (1H,m), 1.61 (6H,s), 1.53 (6H,s), 1.41 (1H,m), 1.35 (9H,s), 1.08 (1H,m), 0.84 (3H,d,J=6.5 Hz), 0.08 (9H,m).

---

I claim:

1. A compound of the formula:

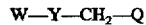

wherein

W is: a farnesyl group, a geranylgeranyl group, a substituted farnesyl group, a substituted geranylgeranyl group or a lipophilic unsaturated hydrocarbon; Y is:

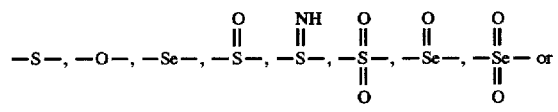

$-CH_2-$; Q is

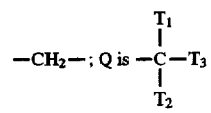

wherein $T_1$ is: H, F, or $-(CH_2)_n-X_1$;

$T_2$ is: $-NHCOCH_3$,

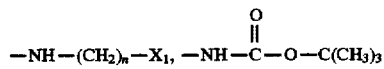

or a peptide of 20 or fewer amino acids; wherein $X_1$ is: $-SH$, $-COOH$, or $-CONH_2$; and n is an integer less than 20;

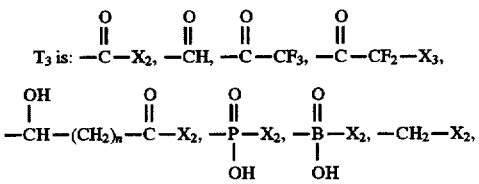

wherein $X_2$ is a peptide of 20 or fewer amino acids linked to carbon via the amino terminal nitrogen of said peptide; $X_3$ is a peptide of 20 or fewer amino acids linked via an alpha carbon of said peptide; and n is an integer less than 20, said compound being characterized by inhibiting enzymatic proteolysis of a peptide having the carboxyl-terminal motif -CAAX (SEQ ID NO: 3) wherein C=cysteine, A=aliphatic amino acid, and X=any amino acid.

2. The compound of claim 1 wherein Y is —S—.

3. The compound of claim 1 wherein $T_1$ is H; $T_2$ is —NHCOCH$_3$, and

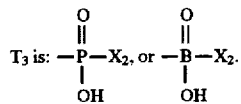

4. The compound of claim 1 wherein $T_1$ is H; $T_2$ is:

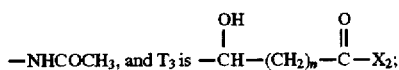

and n is an integer less than three.

5. The compound of claim 1 wherein $T_1$ is H; $T_2$ is —NHCOCH$_3$, and $T_3$ is —CH$_2$—X$_2$.

6. A method for preparing a medicament for inhibiting neoplastic cell growth, said method comprising admixing the inhibitor of claim 1 with a pharmaceutically acceptable carrier.

7. The compound of claim 1 wherein W is farnesyl, Y is —S—,

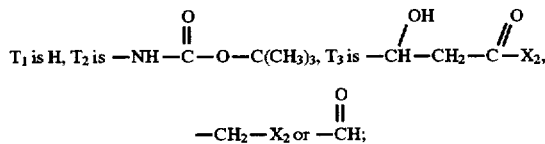

and $X_2$ is a peptide of three or fewer amino acids.

8. The compound of claim 1 having the formula

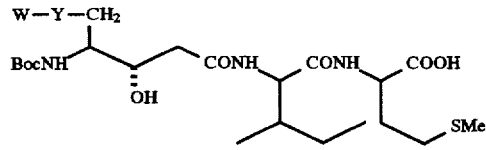

wherein W is farnesyl and Y is —S—.

9. The compound of claim 1 having the formula

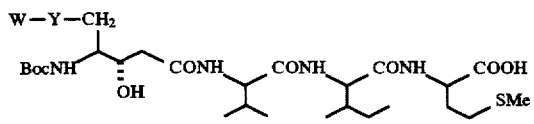

wherein W is farnesyl and Y is —S—.

10. The compound of claim 1 having the formula

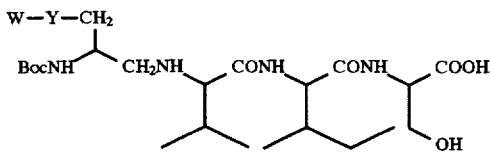

wherein W is farnesyl and Y is —S—.

11. The compound of claim 1 having the formula

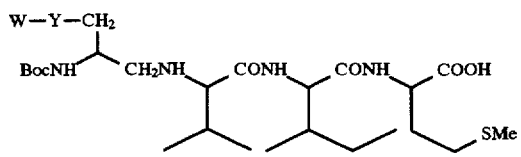

wherein W is farnesyl and Y is —S—.

12. The compound of claim 1 having the formula

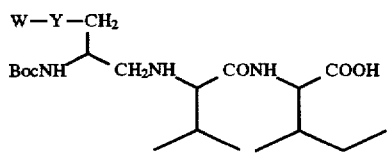

wherein W is farnesyl and Y is —S—.

13. The compound of claim 1 having the formula

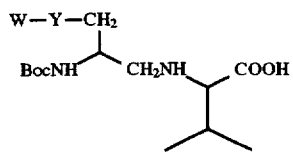

wherein W is farnesyl and Y is —S—.

14. The compound of claim 1 having the formula

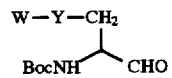

wherein W is farnesyl and Y is —S—.

15. The compound of claim 1 having the formula

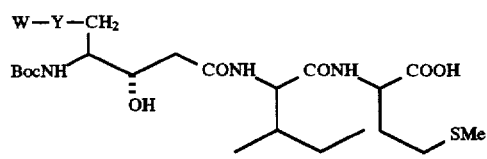

wherein W is farnesyl and Y is —S—.

16. The compound of claim 1 having the formula

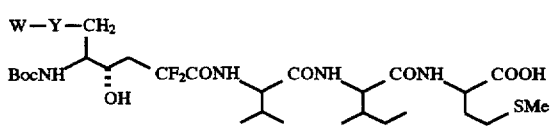

wherein W is farnesyl and Y is —S—.

* * * * *